United States Patent
Sitlani et al.

(10) Patent No.: US 8,263,353 B2
(45) Date of Patent: Sep. 11, 2012

(54) METHOD FOR DETECTING AUTOPROCESSED, SECRETED PCSK9

(75) Inventors: Ayesha Sitlani, Metuchen, NJ (US);
Timothy S. Fisher, Plainsboro, NJ (US);
Joseph C. Santoro, Belle Mead, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 431 days.

(21) Appl. No.: 12/593,342

(22) PCT Filed: Mar. 21, 2008

(86) PCT No.: PCT/US2008/003800
§ 371 (c)(1), (2), (4) Date: Sep. 28, 2009

(87) PCT Pub. No.: WO2008/118386
PCT Pub. Date: Oct. 2, 2008

(65) Prior Publication Data
US 2010/0113575 A1    May 6, 2010

Related U.S. Application Data

(60) Provisional application No. 60/920,191, filed on Mar. 27, 2007.

(51) Int. Cl.
*G01N 33/573* (2006.01)
*G01N 33/567* (2006.01)

(52) U.S. Cl. .......... 435/7.21; 435/7.6; 435/7.1; 435/7.2; 435/7.4

(58) Field of Classification Search .......... None
See application file for complete search history.

(56) References Cited

U.S. PATENT DOCUMENTS

| | | | |
|---|---|---|---|
| 4,703,004 A | 10/1987 | Hopp et al. | |
| 4,782,137 A | 11/1988 | Hopp et al. | |
| 4,851,341 A | 7/1989 | Hopp et al. | |
| 5,011,912 A | 4/1991 | Hopp et al. | |
| 2003/0059811 A1 | 3/2003 | Djaballah et al. | |
| 2003/0119038 A1 | 6/2003 | Bingham et al. | |
| 2004/0009553 A1 | 1/2004 | Glucksmann et al. | |
| 2006/0234242 A1 | 10/2006 | Cheatham et al. | |
| 2009/0130691 A1* | 5/2009 | Seidah et al. ................... 435/7.2 |

FOREIGN PATENT DOCUMENTS

| EP | 1067182 | 1/2001 |
|---|---|---|
| EP | 1440981 | 7/2004 |
| EP | 1471152 | 10/2004 |
| WO | WO 01/31007 | 5/2001 |
| WO | WO 01/34768 | 5/2001 |
| WO | WO 01/57081 | 8/2001 |
| WO | WO 01/77137 | 10/2001 |
| WO | WO 01/98468 | 12/2001 |
| WO | WO 02/14358 | 2/2002 |
| WO | WO 02/46383 | 6/2002 |
| WO | WO 02/046383 | 7/2002 |
| WO | WO 02/090526 | 11/2002 |
| WO | WO 02/102993 | 12/2002 |
| WO | WO 02/102994 | 12/2002 |
| WO | WO 2005/013666 | 2/2005 |

OTHER PUBLICATIONS

Benjannet et al., 2004 J. Biol. Chem. 279:48865-48875.
Molloy et al., 1994 EMBO J. 13:18-33.
Kotowski et al., 2006 Am. J. Hum. Genet 78:410-422.
Leduc et al., 1992 J. Biol. Chem. 267:14303-14308.
Fugere et al., 2002 J. Biol. Chem. 277:7648-7656.
Zhong et al., 1999 J. Biol. Chem. 274:33913-33920.

* cited by examiner

*Primary Examiner* — Sharon Wen

(57) ABSTRACT

The present invention provides a method for detecting autoprocessed, secreted PCSK9, a protein involved in cholesterol homeostasis, and for effectively identifying compounds that inhibit autocleavage and secretion from cells. The disclosed method involves the insertion of an epitope tag into a PCSK9 expression construct immediately C-terminal to the pro domain ending at an amino acid residue corresponding to Q152 of human PCSK9. Upon autoprocessing, the epitope tag is exposed and capable of recognition by anti-epitope antibodies or other suitable identification system, allowing for the selective and exclusive identification and/or quantification of processed PCSK9. The present disclosure thus advances the goal of providing enabling technology to the art for the effective identification of therapeutics effective in combating coronary heart disease.

15 Claims, 12 Drawing Sheets

FIGURE 1

```
ATGGGCACCGTCAGCTCCAGGCGGTCCTGGTGGCCGCTGCCACTGCTGCTGCTGCTGCTGCTCCT
GGGTCCCGCGGGCGCCCGTGCGCAGGAGGACGAGGACGGCGACTACGAGGAGCTGGTGCTAGCCTTGC
GTTCCGAGGAGGACGGCCTGGCCGAAGCACCCGAGCACGGAACCACAGCCACCTTCCACCGCTGCGCC
AAGGATCCGTGGAGGTTGCCTGGCACCTACGTGGTGGTGCTGAAGGAGGAGACCCACCTCTCGCAGTC
AGAGCGCACTGCCCGCCGCCTGCAGGCCCAGGCTGCCCGCCGGGGATACCTCACCAAGATCCTGCATG
TCTTCCATGGCCTTCTTCCTGGCTTCCTGGTGAAGATGAGTGGCGACCTGCTGGAGCTGGCCTTGAAG
TTGCCCCATGTCGACTACATCGAGGAGGACTCCTCTGTCTTTGCCCAGAGCATCCCGTGGAACCTGGA
GCGGATTACCCCTCCACGGTACCGGGCGGATGAATACCAGCCCCCCGACGGAGGCAGCCTGGTGGAGG
TGTATCTCCTAGACACCAGCATACAGAGTGACCACCGGGAAATCGAGGGCAGGGTCATGGTCACCGAC
TTCGAGAATGTGCCCGAGGAGGACGGGACCCGCTTCCACAGACAGGCCAGCAAGTGTGACAGTCATGG
CACCCACCTGGCAGGGGTGGTCAGCGGCCGGGATGCCGGCGTGGCCAAGGGTGCCAGCATGCGCAGCC
TGCGCGTGCTCAACTGCCAAGGGAAGGGCACGGTTAGCGGCACCCTCATAGGCCTGGAGTTTATTCGG
AAAAGCCAGCTGGTCCAGCCTGTGGGGCCACTGGTGGTGCTGCTGCCCCTGGCGGGTGGGTACAGCCG
CGTCCTCAACGCCGCCTGCCAGCGCCTGGCGAGGGCTGGGGTCGTGCTGGTCACCGCTGCCGGCAACT
TCCGGGACGATGCCTGCCTCTACTCCCCAGCCTCAGCTCCCGAGGTCATCACAGTTGGGGCCACCAAT
GCCCAGGACCAGCCGGTGACCCTGGGGACTTTGGGGACCAACTTTGGCCGCTGTGTGGACCTCTTTGC
CCCAGGGGAGGACATCATTGGTGCCTCCAGCGACTGCAGCACCTGCTTTGTGTCACAGAGTGGGACAT
CACAGGCTGCTGCCCACGTGGCTGGCATTGCAGCCATGATGCTGTCTGCCGAGCCGGAGCTCACCCTG
GCCGAGTTGAGGCAGAGACTGATCCACTTCTCTGCCAAAGATGTCATCAATGAGGCCTGGTTCCCTGA
GGACCAGCGGGTACTGACCCCCAACCTGGTGGCCGCCCTGCCCCCCAGCACCCATGGGGCAGGTTGGC
AGCTGTTTTGCAGGACTGTGTGGTCAGCACACTCGGGGCCTACACGGATGGCCACAGCCATCGCCCGC
TGCGCCCCAGATGAGGAGCTGCTGAGCTGCTCCAGTTTCTCCAGGAGTGGGAAGCGGCGGGGCGAGCG
CATGGAGGCCCAAGGGGGCAAGCTGGTCTGCCGGGCCCACAACGCTTTTGGGGGTGAGGGTGTCTACG
CCATTGCCAGGTGCTGCCTGCTACCCCAGGCCAACTGCAGCGTCCACACAGCTCCACCAGCTGAGGCC
AGCATGGGGACCCGTGTCCACTGCCACCAACAGGGCCACGTCCTCACAGGCTGCAGCTCCCACTGGGA
GGTGGAGGACCTTGGCACCCACAAGCCGCCTGTGCTGAGGCCACGAGGTCAGCCCAACCAGTGCGTGG
GCCACAGGGAGGCCAGCATCCACGCTTCCTGCTGCCATGCCCCAGGTCTGGAATGCAAAGTCAAGGAG
CATGGAATCCCGGCCCCTCAGGAGCAGGTGACCGTGGCCTGCGAGGAGGGCTGGACCCTGACTGGCTG
CAGTGCCCTCCCTGGGACCTCCCACGTCCTGGGGGCCTACGCCGTAGACAACACGTGTGTAGTCAGGA
GCCGGGACGTCAGCACTACAGGCAGCACCAGCGAAGAGGCCGTGACAGCCGTTGCCATCTGCTGCCGG
AGCCGGCACCTGGCGCAGGCCTCCCAGGAGCTCCAG [SEQ ID NO: 5]
```

FIGURE 2

```
MGTVSSRRSWWPLPLLLLLLLLLGPAGARAQEDEDGDYEELVLALRSEEDGLAEAPEHGTTATFHRCA
KDPWRLPGTYVVVLKEETHLSQSERTARRLQAQAARRGYLTKILHVFHGLLPGFLVKMSGDLLELALK
LPHVDYIEEDSSVFAQSIPWNLERITPPRYRADEYQPPDGGSLVEVYLLDTSIQSDHREIEGRVMVTD
FENVPEEDGTRFHRQASKCDSHGTHLAGVVSGRDAGVAKGASMRSLRVLNCQGKGTVSGTLIGLEFIR
KSQLVQPVGPLVVLLPLAGGYSRVLNAACQRLARAGVVLVTAAGNFRDDACLYSPASAPEVITVGATN
AQDQPVTLGTLGTNFGRCVDLFAPGEDIIGASSDCSTCFVSQSGTSQAAAHVAGIAAMMLSAEPELTL
AELRQRLIHFSAKDVINEAWFPEDQRVLTPNLVAALPPSTHGAGWQLFCRTVWSAHSGPTRMATAIAR
CAPDEELLSCSSFSRSGKRRGERMEAQGGKLVCRAHNAFGGEGVYAIARCCLLPQANCSVHTAPPAEA
SMGTRVHCHQQGHVLTGCSSHWEVEDLGTHKPPVLRPRGQPNQCVGHREASIHASCCHAPGLECKVKE
HGIPAPQEQVTVACEEGWTLTGCSALPGTSHVLGAYAVDNTCVVRSRDVSTTGSTSEEAVTAVAICCR
SRHLAQASQELQ
[SEQ ID NO: 6]
```

FIGURE 3

MGTVSSRRSWWPLPLLLLLLLLLGPAGARAQEDEDGDYEELVLALRSEEDGLAEAPEHGTT
ATFHRCAKDPWRLPGTYVVVLKEETHLSQSERTARRLQAQAARRGYLTKILHVFHGLLPGFL
VKMSGDLLELALKLPHVDYIEEDSSVFAQDYKDDDDSIPWNLERITPPRYRADEYQPPDGGS
LVEVYLLDTSIQSDHREIEGRVMVTDFENVPEEDGTRFHRQASKCDSHGTHLAGVVSGRDAG
VAKGASMRSLRVLNCQGKGTVSGTLIGLEFIRKSQLVQPVGPLVVLLPLAGGYSRVLNAACQ
RLARAGVVLVTAAGNFRDDACLYSPASAPEVITVGATNAQDQPVTLGTLGTNFGRCVDLFA
PGEDIIGASSDCSTCFVSQSGTSQAAAHVAGIAAMMLSAEPELTLAELRQRLIHFSAKDVINEA
WFPEDQRVLTPNLVAALPPSTHGAGWQLFCRTVWSAHSGPTRMATAIARCAPDEELLSCSSF
SRSGKRRGERMEAQGGKLVCRAHNAFGGEGVYAIARCCLLPQANCSVHTAPPAEASMGTR
VHCHQQGHVLTGCSSHWEVEDLGTHKPPVLRPRGQPNQCVGHREASIHASCCHAPGLECKV
KEHGIPAPQEQVTVACEEGWTLTGCSALPGTSHVLGAYAVDNTCVVRSRDVSTTGSTSEEAV
TAVAICCRSRHLAQASQELQ
[SEQ ID NO: 11]

FIGURE 4

MGTVSSRRSWWPLPLLLLLLLLLGPAGARAQEDEDGDYEELVLALRSEEDGLAEAPEHGTT
ATFHRCAKDPWRLPGTYVVVLKEETHLSQSERTARRLQAQAARRGYLTKILHVFHGLLPGFL
VKMSGDLLELALKLPHVDYIEEDSSVFAQDYKDDDDSIPWNLERITPPRYRADEYQPPDGGS
LVEVYLLDTSIQSDHREIEGRVMVTDFENVPEEDGTRFHRQASKCDSHGTHLAGVVSGRDAG
VAKGASMRSLRVLNCQGKGTVSGTLIGLEFIRKSQLVQPVGPLVVLLPLAGGYSRVLNAACQ
RLARAGVVLVTAAGNFRDDACLYSPASAPEVITVGATNAQDQPVTLGTLGTNFGRCVDLFA
PGEDIIGASSDCSTCFVSQSGTSQAAAHVAGIAAMMLSAEPELTLAELRQRLIHFSAKDVINEA
WFPEDQRVLTPNLVAALPPSTHGAGWQLFCRTVWSAHSGPTRMATAIARCAPDEELLSCSSF
SRSGKRRGERMEAQGGKLVCRAHNAFGGEGVYAIARCCLLPQANCSVHTAPPAEASMGTR
VHCHQQGHVLTGCSSHWEVEDLGTHKPPVLRPRGQPNQCVGHREASIHASCCHAPGLECKV
KEHGIPAPQEQVTVACEEGWTLTGCSALPGTSHVLGAYAVDNTCVVRSRDVSTTGSTSEEAV
TAVAICCRSRHLAQASQELQKGNSADIQHSGGRSSLEGPRFEGKPIPNPLLGLDSTRTGHH
HHHH
[SEQ ID NO: 12]

METHOD FOR DETECTING AUTOPROCESSED, SECRETED PCSK9

CROSS-REFERENCE TO RELATED APPLICATIONS

This application claims the benefit of U.S. Provisional Application No. 60/920,191 filed on Mar. 27, 2007.

STATEMENT REGARDING FEDERALLY-SPONSORED R&D

Not Applicable

REFERENCE TO MICROFICHE APPENDIX

Not Applicable

FIELD OF THE INVENTION

The present invention discloses an effective method for detecting autoprocessed, secreted PCSK9, a protein which in its processed form is believed to be involved in cholesterol homeostasis. The disclosed method and constructs enable the skilled artisan to accurately and effectively study PCSK9 autoprocessing and, importantly, allows the skilled artisan to screen for modulators effective in the inhibition of PCSK9 processing and the treatment of cholesterol-associated inflections or conditions. The method entails inserting an epitope tag into a PCSK9 expression construct immediately C-terminal to the pro domain ending at an amino acid residue corresponding to Q152 of human PCSK9. Upon autoprocessing of the expressed PCSK9, the epitope tag is exposed and capable of recognition by anti-epitope antibodies or other suitable identification system. The described methods allow for the specific detection of processed PCSK9.

BACKGROUND OF THE INVENTION

Proprotein convertase subtilisin-kexin type 9 (hereinafter called "PCSK9"), also known as neural apoptosis-regulated convertase 1 ("NARC-1"), is a proteinase K-like subtilase identified as the $9^{th}$ member of the secretory subtilase family; see Seidah et al., 2003 *PNAS* 100:928-933. The gene for PCSK9 localizes to human chromosome 1p33-p34.3; Seidah et al., supra. PCSK9 is expressed in cells capable of proliferation and differentiation including, for example, hepatocytes, kidney mesenchymal cells, intestinal ileum, and colon epithelia as well as embryonic brain telencephalon neurons; Seidah et al., supra.

Original synthesis of PCSK9 is in the form of an inactive enzyme precursor, or zymogen, of ~72-kDa which undergoes autocatalytic, intramolecular processing in the endoplasmic reticulum ("ER") to activate its functionality. This internal processing event has been reported to occur at the SSVFAQ↓SIPWNL158 (SEQ ID NOs: 31 and 36, respectively) motif rendering the first three N-terminal residues Ser-Ile-Pro (Benjannet et al., 2004 *J. Biol. Chem.* 279:48865-48875), and has been reported as a requirement of exit from the ER; Benjannet et al., supra; Seidah et al., supra. The cleaved protein is then secreted. The cleaved peptide remains associated with the activated and secreted enzyme; supra.

The protein sequence for human PCSK9, which is ~22-kb long with 12 exons encoding a 692 amino acid protein, can be found, for example, at Deposit No. NP_777596.2. Human, mouse and rat PCSK9 nucleic acid sequences have been deposited; see, e.g., GenBank Accession Nos.: AX127530 (also AX207686), NP 705793 (also Q80W65), and P59996, respectively. PCSK9 possesses several domains found in other proprotein convertases, including an N-terminal signal sequence, a pro domain, a catalytic domain and a cysteine-rich C-terminal domain. The PCSK9 catalytic domain shares high sequence similarity with the proteinase K family of subtilases and contains a catalytic triad (D186, H226 and S386).

PCSK9 is disclosed and/or claimed in several patent publications including, but not limited to the following: PCT Publication Nos. WO 01/31007, WO 01/57081, WO 02/14358, WO 01/98468, WO 02/102993, WO 02/102994, WO 02/46383, WO 02/90526, WO 01/77137, and WO 01/34768; US Publication Nos. US 2004/0009553 and US 2003/0119038, and European Publication Nos. EP 1 440 981, EP 1 067 182, and EP 1 471 152.

PCSK9 has been ascribed a role in the differentiation of hepatic and neuronal cells (Seidah et al., supra.), is highly expressed in embryonic liver, and has been strongly implicated in cholesterol homeostasis. Recent studies seem to suggest a specific role in cholesterol homeostasis or uptake. In a study of cholesterol-fed rats, Maxwell et al. found that PCSK9 was downregulated in a similar manner as three other genes involved in cholesterol biosynthesis, Maxwell et al., 2003 *J. Lipid Res.* 44:2109-2119. Interestingly, as well, the expression of PCSK9 was determined to be regulated by sterol regulatory element-binding proteins ("SREBP"), as seen with other genes involved in cholesterol metabolism; supra. These findings were later supported by a study of PCSK9 transcriptional regulation which demonstrated that such regulation was quite typical of other genes implicated in lipoprotein metabolism; Dubuc et al., 2004 *Arterioscler. Thromb. Vasc. Biol.* 24:1454-1459. PCSK9 expression was determined to be upregulated by statins in a manner attributed to the cholesterol-lowering effects of the drugs; supra. Additionally, PCSK9 promoters were found to possess two conserved sites involved in cholesterol regulation, a sterol regulatory element and an Sp1 site; supra.

Several lines of evidence demonstrate that PCSK9, in particular, lowers the amount of hepatic LDLR protein and thus compromises the liver's ability to remove LDL cholesterol from the circulation. Adenovirus-mediated overexpression of PCSK9 in the livers of mice results in the accumulation of circulating LDL-C due to a dramatic loss of hepatic LDLR protein, with no effect of LDLR mRNA levels; Benjannet et al., 2004 *J. Biol. Chem.* 279:48865-48875; Maxwell & Breslow, 2004 *PNAS* 101:7100-7105; Park et al., 2004 *J. Biol. Chem.* 279:50630-50638; and Lalanne et al., 2005 *J. Lipid Res.* 46:1312-1319. The effect of PCSK9 overexpression on raising circulating LDL-C levels in mice is completely dependent on the expression of LDLR, again, indicating that the regulation of LDL-C by PCSK9 is mediated through down-regulation of LDLR protein. In agreement with these findings, mice lacking PCSK9 or in which PCSK9 mRNA has been lowered by antisense oligonucleotides inhibitors have higher levels of hepatic LDLR protein and a greater ability to clear circulating LDL-C; Rashid et al., 2005 *PNAS* 102:5374-5379; and Graham et al., 2007 *J. Lipid Res.* C600025-JLR600200Jan. 2, 2007 (epublication number). In addition, lowering PCSK9 levels in cultured human hepatocytes by siRNA also results in higher LDLR protein levels and an increased ability to take up LDL-C; Benjannet et al., 2004 *J. Biol. Chem.* 279:48865-48875; and Lalanne et al., 2005 *J. Lipid Res.* 46:1312-1319. Together, these data indicate that PCSK9 action leads to increased LDL-C by lowering LDLR protein levels.

A number of mutations in the gene PCSK9 have also been conclusively associated with autosomal dominant hypercholesterolemia ("ADH"), an inherited metabolism disorder characterized by marked elevations of low density lipoprotein ("LDL") particles in the plasma which can lead to premature cardiovascular failure; see Abifadel et al., 2003 *Nature Genetics* 34:154-156; Timms et al., 2004 *Hum. Genet.* 114:349-353; Leren, 2004 *Clin. Genet.* 65:419-422. A later-published study on the S127R mutation of Abifadel et al., supra, reported that patients carrying such a mutation exhibited higher total cholesterol and apoB100 in the plasma attributed to (1) an overproduction of apoB100-containing lipoproteins, such as low density lipoprotein ("LDL"), very low density lipoprotein ("VLDL") and intermediate density lipoprotein ("IDL"), and (2) an associated reduction in clearance or conversion of said lipoproteins; Ouguerram et al., 2004 *Arterioscler. Thromb. Vasc. Biol.* 24:1448-1453.

Accordingly, there can be no doubt that PCSK9 plays a role in the regulation of LDL. The expression or upregulation of PCSK9 is associated with increased plasma levels of LDL cholesterol, and the corresponding inhibition or lack of expression of PCSK9 is associated with low LDL cholesterol plasma levels. In addition, lower levels of LDL cholesterol associated with sequence variations in PCSK9 have been found to confer protection against coronary heart disease; Cohen, 2006 *N. Engl. J. Med.* 354:1264-1272.

The identification of compounds and/or agents effective in the treatment of cardiovascular affliction is, thus, highly desirable. Reductions in LDL cholesterol levels have been shown through clinical trials to be directly related to the rate of coronary events; Law et al., 2003 *BMJ* 326:1423-1427. More recently, the moderate lifelong reduction in plasma LDL cholesterol levels was found to correlate with a substantial reduction in the incidence of coronary events; Cohen et al., supra. This was the case even in populations with a high prevalence of non-lipid-related cardiovascular risk factors; supra. Accordingly, there is great benefit to be reaped from the managed control of LDL cholesterol levels.

The present invention advances these interests by providing an effective method for screening compounds/agents of use in the antagonism of PCSK9. Such compounds should be effective in the management of serum LDL cholesterol levels.

SUMMARY OF THE INVENTION

The present invention relates to a method for identifying and/or quantifying autoprocessed, secreted proprotein convertase subtilisin-kexin type 9 ("PCSK9"), a protein involved in cholesterol homeostasis, to the exclusion of nonprocessed, secreted PCSK9 in cell supernatant. The method entails the insertion of an epitope tag into a PCSK9 expression construct immediately C-terminal to the pro domain ending at Q152. Upon autoprocessing, the epitope tag is exposed at the N-terminus of the mature protein and capable of recognition by anti-epitope antibodies or other suitable identification system. This allows for the selective identification and/or quantification of processed PCSK9. This method, further, allows for the effective identification and analysis of agents including biological and chemical agents capable of stimulating and/or inhibiting autocleavage and secretion from cells. The present disclosure, thus, advances the goal of providing enabling technology to the art for the effective identification of therapeutics of use in combating coronary heart disease.

The present invention relates as well to isolated nonprocessed, secreted PCSK9.

The present invention further relates to methods for interfering with the processing of PCSK9, comprising expressing nucleic acid encoding the pro domain of PCSK9 in a cell, cell population, or subject of interest.

BRIEF DESCRIPTION OF THE DRAWINGS

FIG. 1 illustrates nucleic acid (SEQ ID NO: 5) encoding wild-type human PCSK9.

FIG. 2 illustrates an amino acid sequence (SEQ ID NO: 6) for wild-type human PCSK9.

FIG. 3 illustrates an amino acid sequence (SEQ ID NO: 11) for PCSK9-152 FLAG.

FIG. 4 illustrates an amino acid sequence (SEQ ID NO: 12) for PCSK9-152 FLAG-V5/His.

FIG. 12 illustrates the processing of D186A protein after secretion into the media. This is indicated by the change over time in the ratio of unprocessed:processed D186A, with less unprocessed and more processed protein accumulating. PCSK9 secretion was allowed for 2 hours, at which point the media was removed from cells and incubated at 37 degrees for the indicated periods of time. PCSK9 was detected by western blot using an anti-V5 primary antibody and anti-mouse secondary antibody. The lanes in the blot analysis are as follows: (1) 2 hr samples; (2) 6 hr incubation, (3) 18 hr incubation, (4) 42 hr incubation and (6) 66 hr incubation.

DETAILED DESCRIPTION OF THE INVENTION

Figure 5:
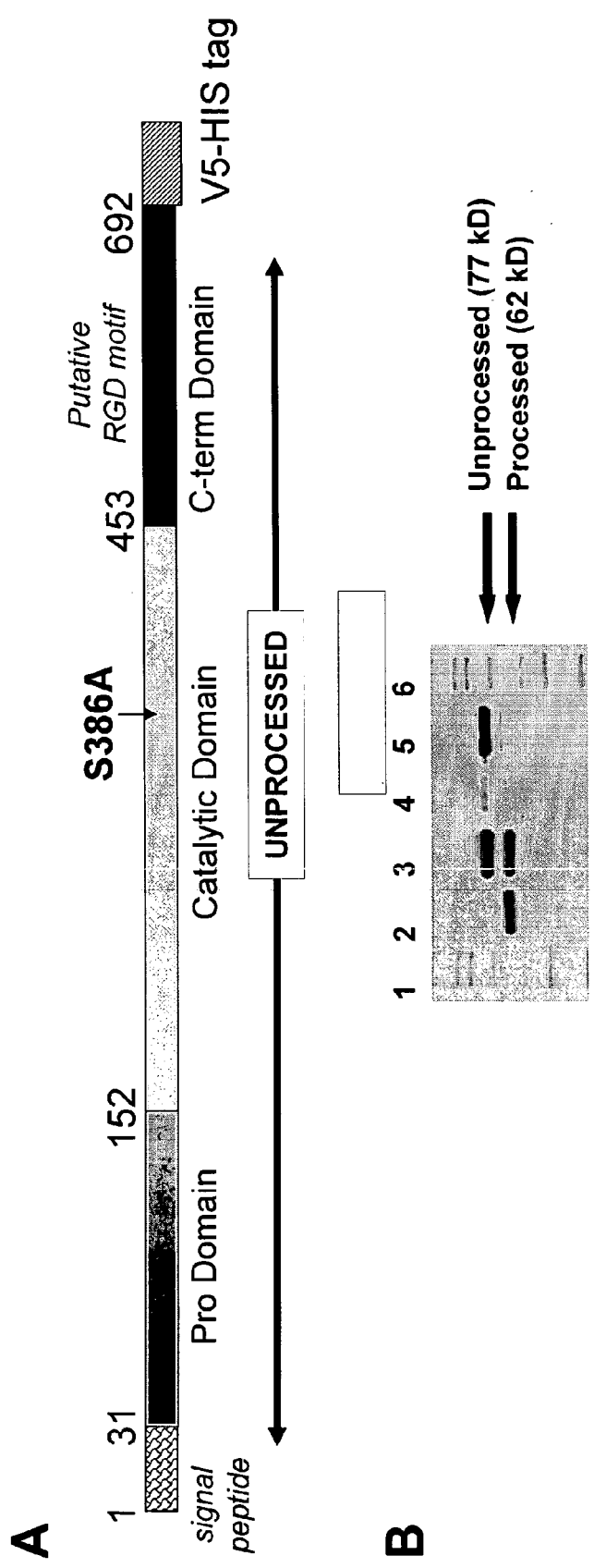
FIGS. 5A and 5B illustrate, respectively, a PCSK9 construct carrying a C-terminal V5/His tag and a western blot analysis from a stable cell line expressing PCSK9-V5/His and PCSK9-V5/His-S386A. The western blot used an anti-V5 primary antibody and anti-mouse IgG secondary antibody for detection. As indicated by the arrows on the right-hand side of the blot, wild-type PCSK9 is present as both nonprocessed and autoprocessed in cell lysate, whereas only autoprocessed PCSK9 is secreted. Notably, Applicants found that, while S386A PCSK9 is not processed, a detectable amount of nonprocessed protein is secreted. The lanes in the blot analysis are as follows: (1) Marker; (2) Wt media (secreted); (3) Wt cell lysate; (4) S386A media (secreted); (5) S386A cell lysate; and (6) Marker.

The present invention relates to a method for identifying and/or quantifying processed, secreted proprotein convertase subtilisin-kexin type 9 ("PCSK9") to the exclusion of nonprocessed, secreted PCSK9 in cell supernatant. Development of the above assay was prompted by Applicants' discovery that mutants of PCSK9 are secreted in a nonprocessed form. Through an extension of these findings, Applicants were, further, able to isolate secreted, nonprocessed PCSK9.

The disclosed methodology entails transforming cells with an expression construct comprising nucleic acid encoding PCSK9 wherein an epitope tag is inserted immediately subsequent to nucleic acid encoding residue "Q" in the stretch of amino acids "FAQ", said series of amino acids roughly corresponding to amino acid residues 150-152 in human PCSK9, amino acid residues 153-155 in murine PCSK9, amino acid residues 149-151 in rat PCSK9 and/or corresponding residues in PCSK9 of another species. In specific embodiments, human PCSK9 is that of SEQ ID NO: 6, murine PCSK9 is that of SEQ ID NO: 18, and rat PCSK9 is that of SEQ ID NO: 19. In further specific embodiments, the PCSK9 employed comprises a mutation in one or more of the catalytic triad residues (D186, H226, S386). In specific embodiments, the PCSK9 employed is that of SEQ ID NO: 34 or SEQ ID NO: 35. To recognize the epitope, an antibody or anti-epitope molecule is introduced into the cell supernatant. The specific antibody or anti-epitope molecule employed should be capable of recognizing the epitope tag only when located at the extreme N (amino)-terminus. The antibody or anti-epitope molecule should, furthermore, bear a selectable marker to enable the ready detection thereof. Bound antibody or anti-epitope molecule is then measured. By means of the above process, the readout is specifically tailored to processed, secreted PCSK9 in the cell supernatant.

Incorporating the epitope tag in this particular location avoids the nonselective recognition of nonprocessed, secreted PCSK9, thus enabling an efficient method to specifically and exclusively evaluate autoprocessed, secreted PCSK9 and effects thereon. Inclusion into this region was, furthermore, notably found not to negatively impact processing and was ultimately well accepted. These findings enabled the development of the methods described herein. The methods, in contrast to the available methods for evaluating PCSK9 processing, are suitable for large scale screening of modulators of PCSK9 processing. The described methods capitalize on Applicants' findings that nonprocessed PCSK9 forms are, in fact, secreted in the media and, in specific embodiments, subsequently processed.

The described methods, further, capitalize on Applicants' findings that PCSK9 can accept, without impact, an insertion in this particular region. The described methods, lastly, capitalize on Applicants' findings with mutant D186A that nonprocessed, secreted PCSK9 is significantly less potent in downregulating LDLR function, in direct contrast to processed PCSK9 which is able to downregulate LDLR function.

The described method is well suited and extremely effective for screening compounds or biologies capable of promoting or, conversely, antagonizing PCSK9 processing, preferably, by greater than 10%, 20%, 30%, 40%, 50%, 60%, 70%, 80%, 90%, and 100%, in that order. This is of significant value given that nonprocessed PCSK9 has been found to be significantly (~20-fold) less active than processed PCSK9 in PCSK9-dependent LDL uptake; see FIG. 11C. Compounds or biologicals capable of antagonizing PCSK9 processing should be useful in the treatment of conditions associated with or impacted by PCSK9 function, including, but not limited to hypercholesterolemia, coronary heart disease, metabolic syndrome, acute coronary syndrome and related conditions. In specific embodiments, PCSK9 processing antagonists should be effective in lowering plasma LDL cholesterol levels.

Nucleic acid encoding PCSK9 of use in the methods disclosed herein is any nucleic acid encoding PCSK9, known mutants or equivalents thereof, or any protein with at least 80% homology to PCSK9 at the amino acid level having either conservative amino acid substitutions or modifications thereto; said protein which exhibits PCSK9-attributed function such as, for example, measurable inhibition of LDL uptake by the LDL receptor. The nucleic acid may include DNA (inclusive of cDNA) and/or RNA. Nucleic acids of the present invention may be obtained using standard molecular biology techniques. Nucleic acid of use herein should hybridize to the complement of nucleic acid encoding native PCSK9 (human, mouse, rat, or other species of PCSK9) under stringent hybridization conditions. Methods for hybridizing nucleic acids are well-known in the art; see, e.g., Ausubel, *Current Protocols in Molecular Biology*, John Wiley & Sons, N.Y., 6.3.1-6.3.6, 1989. For purposes of exemplification and not limitation, moderately stringent hybridization conditions may, in specific embodiments, use a prewashing solution containing 5× sodium chloride/sodium citrate (SSC), 0.5% w/v SDS, 1.0 mM EDTA (pH 8.0), hybridization buffer of about 50% v/v formamide, 6×SSC, and a hybridization temperature of 55° C. (or other similar hybridization solutions, such as one containing about 50% v/v formamide, with a hybridization temperature of 42° C.), and washing conditions of 60° C., in 0.5×SSC, 0.1% w/v SDS. For purposes of exemplification and not limitation, stringent hybridization conditions may, in specific embodiments, use the following conditions: 6×SSC at 45° C., followed by one or more washes in 0.1×SSC, 0.2% SDS at 68° C. One of skill in the art may, furthermore, manipulate the hybridization and/or washing conditions to increase or decrease the stringency of hybridization such that nucleic acids comprising nucleotide sequences that are at least 80, 85, 90, 95, 98, or 99% identical to each other typically remain hybridized to each other. The basic parameters affecting the choice of hybridization conditions and guidance for devising suitable conditions are set forth by Sambrook et al., *Molecular Cloning: A Laboratory Manual*, Cold Spring Harbor Laboratory Press, Cold Spring Harbor, N.Y., chapters 9 and 11, 1989 and Ausubel et al. (eds), *Current Protocols in Molecular Biology*, John Wiley & Sons, Inc., sections 2.10 and 6.3-6.4, 1995. Such parameters can be readily determined by those having ordinary skill in the art based on, for example, the length and/or base composition of the DNA.

Nucleic acid encoding PCSK9 should comprise an epitope tag immediately C-terminal to the pro domain ending at the amino acid residue corresponding to Q152 (human), Q 155 (murine), Q 151 (rat), or corresponding residue in PCSK9 of another species. The epitope tag should be recognized by an antibody or other epitope-specific molecule only when exposed at the extreme amino-terminus. In this manner, the tag will only result in a signal when the PCSK9 molecule is processed. One specific example of an epitope tag of use in the methods of the present invention is the FLAG tag. When used in conjunction with the ANTI-FLAG M 1 antibody, the FLAG tag is recognized when located exclusively at the extreme amino-terminus, thus enabling its detection only when PCSK9 has been processed. As one of skill in the art will readily appreciate, the invention may be practiced with any tag/anti-tag combination that allows for the selective identification of an exposed N-terminus. The anti-tag function may be carried out by any antibody or anti-epitope molecule that specifically and distinctly recognizes and binds to the epitope.

Detection of the epitope-antibody or epitope-anti-epitope interaction may be accomplished by labeling the antibody or anti-epitope molecule with a selectable marker. Any marker capable of emitting some form of recognizable signal, or possessing some recognizable element, is suitable for use in the methods of the present invention. For purposes of illustration and not limitation, some selectable markers of use are alkaline phosphatase, radioactive isotopes, a lanthanide such as Europium (e.g, Eu3+), XL665, a fluorescent moiety, a quencher moiety, a chemiluminescent moiety, biotin, and biotin derivatives. Accordingly, methods employing such labeled molecules form specific embodiments hereof.

One or more labels, which may be the same or different, may be present on one or both sides of the processing site. The present invention, in fact, encompasses such methods where an additional epitope tag is inserted into the PCSK9 sequence. Use of multiple labels allows for the independent recognition of total processed and nonprocessed PCSK9. In specific embodiments, the additional epitope tag may be inserted in the signal peptide region. In other embodiments, the additional epitope tag is inserted subsequent to amino acid residue S corresponding to S153 in human PCSK9; S156 in murine PCSK9, S152 in rat PCSK9 and/or corresponding residue of PCSK9 in another species. Placement of the additional epitope(s) should be selected so as not to significantly affect PCSK9 processing. As the skilled artisan is aware, the effect of any particular epitope on processing may be readily evaluated by assaying for processing. In specific embodiments, the epitope tag is inserted at the C-terminus of PCSK9.

Detection of the additional epitope(s) in these specific embodiments may be accomplished through the introduction of additional antibody(ies) or anti-epitope molecule(s) into the cell supernatant. The antibody(ies) or anti-epitope(s) molecules must be capable of recognizing the additional epitope tag(s) and, further, bear a selectable marker capable of independent detection and/or measurement. Total processed and nonprocessed PCSK9 may then be determined by detection and/or measurement of bound antibody or anti-epitope molecule carrying the selectable marker. In specific embodiments, the epitope tag is a V5/His6X tag. In specific embodiments where a V5/His6X tag is utilized, the antibody introduced to detect the tag is an anti-His antibody. In specific embodiments, the antibody is an XL665-labeled anti-His antibody.

In homogenous formats, multiple labels may interact such that signal will increase or decrease upon PCSK9 processing. These formats as all variations of the methods described herein form specific embodiments of the present invention. An example of a homogeneous signal increase format is an assay employing an internally quenched FRET pair. An acceptor and donor FRET pair present on different sites of PCSK9 produces a different signal depending upon whether processing has taken place. In the absence of processing, a donor excited by a suitable light source emits energy having the proper wavelength to be absorbed by the acceptor. The acceptor quenches signal production from the donor by either emitting light at a different wavelength (if the acceptor is another fluorophore) or by dissipating the energy to the environment (if the acceptor is a quencher). FRET assays can be run assaying for the appearance of donor fluorescence if the acceptor is a quencher and, upon processing, donor and quencher are separated. Alternatively, if both donor and acceptor are fluorophores and the donor is being excited, FRET assays can be run assaying for the appearance of donor fluorescence or the disappearance of acceptor fluorescence. Accordingly, the present invention encompasses methods as disclosed herein where the antibody or anti-epitope molecule and additional antibody or anti-epitope molecule have fluorophores as their selectable markers, and detection and/or measurement of bound antibody or anti-epitope molecule is through detection of fluorescence resonance energy transfer between the fluorophores on the antibodies or anti-epitope molecules. In specific embodiments, the antibody or anti-epitope molecule and additional antibody or anti-epitope molecule are labeled with an acceptor and a donor fluorescence resonance energy transfer pair.

A variety of different fluorophores and quenchers are well known in the art. Examples of suitable fluorophores include dansyl and its derivatives, fluorescein and its derivatives, rhodamine and its derivatives, Texas Red, coumarin derivatives, Cy dyes, AlexaFluor dyes (Molecular Probes), and BODIPY dyes (Molecular Probes). Examples of quenchers includes the QSY series (Molecular Probes), Dabcyl, p-nitrophenyl derivatives, dinitrophenyl derivatives, and the Cy quencher dyes (Amersham-Pharmacia). Techniques and reagents for performing FRET-type assays are well known in the art; see, e.g., Selvin, 2000 *Nat. Struct. Biol.* 7(9):730-734; Clegg, 1995 *Curr. Opin. Biotechnol.* 6(1):103-110; and Wu et al., 1994 *Anal. Biochem.* 218(1):1-13.

With appropriately labeled substrates, alternate technologies may also be used to measure PCSK9 processing and such methods are contemplated as specific embodiments herein. Examples of homogeneous formats include fluorescence polarization, time resolved FRET, SPA™, FlashPlate™, and AlphaScreen™. Examples of heterogeneous formats include DELFIA™, chemiluminescence plate based assays, HPLC, radioactive filter binding assays, absorbance assays, and fluorescence assays.

As one skilled in the art will readily appreciate, the particular assay(s) employed will depend on the readout desired and the epitope tag employed. Following selection of the appropriate epitope tag and the incorporation or affixation of the tag into the nucleic acid encoding PCSK9, the nucleic acid is then transfected into cells by any method capable of effecting the delivery and expression of the PCSK9 transgene.

In specific embodiments, nucleic acid may be delivered to the cells by an expression construct or vector. Vectors of use in the methods of the present invention include, but are not limited to, plasmids and other expression constructs suitable for the expression of the desired PCSK9 protein at the appropriate level for the intended purpose; see, e.g., Sambrook & Russell, *Molecular Cloning: A Laboratory Manual: 3rd Edition*, Cold Spring Harbor Laboratory Press. For most cloning purposes, DNA vectors may be used. Typical vectors include plasmids, modified viruses, bacteriophage, cosmids, yeast artificial chromosomes, and other forms of episomal or integrated DNA. It is well within the purview of the skilled artisan to determine an appropriate vector for the transfer of the nucleic acid. In specific embodiments, in addition to the nucleic acid encoding PCSK9, the vector may also contain an origin of replication for autonomous replication in a host cell, appropriate regulatory sequences, such as a promoter, a termination sequence, a polyadenylation sequence, an enhancer sequence, a selectable marker, a limited number of useful restriction enzyme sites, other sequences as appropriate and the potential for high copy number. If desired, the nucleic acid may be integrated into the host chromosome using techniques well known in the art; see, e.g., Ausubel, *Current Protocols in Molecular Biology*, John Wiley & Sons, 1999, and Marks et al., International Application Number WO 95/17516. Nucleic acid may also be expressed on plasmids maintained episomally or incorporated into an artificial chromosome; see, e.g., Csonka et al., 2000 *J. Cell Science* 113:3207-3216; Vanderbyl et al., 2002 *Molecular Therapy* 5:10.

Methods of subcloning nucleic acid molecules of interest into expression vectors and methods of transforming or transfecting host cells containing the vectors comprising the steps of introducing the respective expression vector into a host cell, and cultivating the host cell under appropriate conditions are well known. The specific technique employed for the introduction of nucleic acid into cells of interest will depend on the type of cell being used. General techniques include, but are not limited to, calcium phosphate transfection, DEAE-Dextran, electroporation, liposome-mediated transfection and transduction using viruses appropriate to the cell line of interest (e.g., retrovirus, vaccinia, baculovirus, or bacteriophage). Cells of use in the methods of the present invention encompass any cells capable of expressing the transgene (PCSK9 with epitope) and include, but are not limited to, the following cells: HEK cells, HepG2 cells and CHO cells. Reference to "cell supernatant" throughout is meant to encompass any and all fluid surrounding cells which express PCSK9 including, but not limited to, cell media, serum and plasma.

In specific embodiments, the methods disclosed herein are used for the identification and screening of antagonists or agonists of PCSK9 processing. Methods for identifying antagonists or agonists of PCSK9 processing entail transforming cells with an expression construct comprising nucleic acid encoding PCSK9 wherein an epitope tag is inserted immediately subsequent to nucleic acid encoding residue "Q" in the stretch of amino acids "FAQ", said series of amino acids roughly corresponding to amino acid residues 150-152 in human PCSK9, amino acid residues, 153-155 in murine PCSK9, amino acid residues 149-151 in rat PCSK9, and/or corresponding residues in PCSK9 of another species. A candidate antagonist or agonist is introduced into the cell supernatant as well as an antibody or anti-epitope molecule bearing a selectable marker which is capable of recognizing the epitope tag only when located at the extreme amino-terminus. The selectable marker must be able to be detected and/or measured. Processed, secreted PCSK9 is specifically determined by detecting and/or measuring bound antibody or anti-epitope molecule carrying the selectable marker. The levels of bound antibody or anti-epitope molecule are compared with levels of bound antibody or anti-epitope molecule obtained from a sample which is not contacted with the candidate antagonist or agonist. Decreased levels of bound antibody or anti-epitope molecule indicate an antagonist of PCSK9 processing. Increased levels of bound antibody or anti-epitope molecule, by contrast, indicate an agonist of PCSK9 processing.

Additional methods of carrying out the present invention employ an expression construct comprising nucleic acid encoding PCSK9 which comprises: (i) a first epitope tag inserted immediately subsequent to nucleic acid encoding residue "Q" in the stretch of amino acid residues "FAQ", said series of amino acids roughly corresponding to amino acid residues 150-152 in human PCSK9, amino acid residues 153-155 in murine PCSK9, amino acid residues 149-151 in rat PCSK9 and/or corresponding residues in PCSK9 of another species and (ii) a second epitope tag inserted in the signal peptide region or subsequent to amino acid residue "S" corresponding to S153 in human PCSK9, S156 in murine PCSK9, S152 in rat PCSK9, and/or corresponding residue in PCSK9 of another species to enable the independent recognition of total processed and nonprocessed PCSK9. A candidate antagonist or agonist is then introduced into the cell supernatant in addition to (i) a first antibody or anti-epitope molecule bearing a selectable marker which is capable of recognizing the first epitope tag only when located at the extreme amino-terminus and (ii) a second antibody or anti-epitope molecule bearing a selectable marker which is capable of recognizing the second epitope tag. The selectable markers must be able to be independently detected and/or measured. Processed, secreted PCSK9 is determined by detecting and/or measuring bound antibody or anti-epitope molecule carrying the selectable marker which recognizes the first epitope tag. Levels of bound antibody or anti-epitope molecule are then compared with that obtained from a sample that was not contacted with the candidate antagonist or agonist. Where the candidate molecule is an antagonist of processing, one would expect to see lower levels of processed PCSK9 secreted and, thus, lower levels of bound first antibodies or anti-epitope molecules as compared to the control (i.e., a sample without test compound). By contrast, where the candidate molecule is an agonist of processing, one would expect to see increased levels of processed PCSK9 secreted. Accordingly, one would expect to see higher levels of bound first antibodies or anti-epitope molecules as compared with the control. In the instance where fluorescence energy transfer is detected between the first and second antibodies or anti-epitope molecules, one would expect, in specific embodiments, the amount of FRET to increase with an agonist of PCSK9 processing and decrease with an antagonist of PCSK9 processing.

Further disclosed herein is a method for identifying and/or quantifying processed, secreted PCSK9 to the exclusion of nonprocessed, secreted PCSK9 in cell supernatant obtained from a transgenic non-human animal transfected with nucleic acid encoding PCSK9. The method entails collecting cell supernatant from an animal that has been transfected with an expression construct comprising nucleic acid encoding PCSK9 wherein an epitope tag is inserted immediately subsequent to nucleic acid encoding residue "Q" in the stretch of amino acid residues "FAQ", said series of amino acids roughly corresponding to amino acid residues 150-152 in human PCSK9, amino acid residues 153-155 in murine PCSK9, amino acid residues 149-151 in rat PCSK9 and/or corresponding residues in PCSK9 of another species. An antibody or suitable anti-epitope molecule is introduced into the cell supernatant. The antibody or anti-epitope molecule should be capable of recognizing the epitope tag only when located at the extreme amino-terminus. The antibody or anti-epitope molecule should, furthermore, bear a selectable marker which can be detected and/or measured. Processed, secreted PCSK9 may then be determined by detecting and/or measuring bound antibody or anti-epitope molecule carrying the selectable marker. Bound antibody or anti-epitope molecule indicating processed, secreted PCSK9/.

The present disclosure also relates to isolated nonprocessed, secreted PCSK9. The discovery that processing-defective or processing-impaired mutants of PCSK9 (and in particular embodiments, PCSK9 mutants S386A and D186A) are in fact secreted in the media in nonprocessed form has enabled the purification and study of nonprocessed, secreted PCSK9. "Isolated" as used herein describes a property that makes the protein different from that found in nature. The difference can be, for example, that it is of a different purity than that found in nature, or of a different structure, or form part of a different structure, than that found in nature. A structure not found in nature, for example, includes nonprocessed, secreted PCSK9 substantially free of other cellular material. In specific embodiments, the isolated nonprocessed, secreted PCSK9 is purified. In preferred embodiments, the PCSK9 is substantially free of other proteins that surround it in its native environment.

Isolated nonprocessed, secreted PCSK9 is of utility in the study of PCSK9 processing, and in the study of antagonists and agonists of such processing. Prior to isolation of the secreted form, Applicants were unable to isolate nonprocessed PCSK9 in the cellular lysate. Because it was not known that PCSK9 was secreted in a nonprocessed form, it was not known that one could purify such form from cell media. The identification of secreted, nonprocessed PCSK9 has, thus, enabled the purification of such a form of PCSK9. From this advance, Applicants have already discovered that some PCSK9 mutants undergo some degree of processing outside the cell; as was determined with PCSK9 mutant D186A (see FIG. 12). Applicants have, furthermore, discovered that processed D186A, not nonprocessed, is able to downregulate LDLR function, indicating that processing, not protease activity of PCSK9, is required for its function after secretion. Isolated nonprocessed, secreted PCSK9, thus, enables a more in-depth evaluation of the effect of environment and added factors (including biologicals and chemicals) on PCSK9 processing.

Accordingly, the present invention encompasses in specific embodiments isolated nonprocessed, secreted PCSK9. Isolated nonprocessed, secreted PCSK9 may be obtained by various methods available to, and readily familiar, to the skilled artisan, including without limitation, purification by standard chromatographic methods such as metal chelate affinity (Ni-NTA, TALON) size exclusion, anion or cation exchange, or other such methods. In specific embodiments, the isolated nonprocessed, secreted PCSK9 is of SEQ ID NO: 6, SEQ ID NO: 18, SEQ ID NO: 19, or derivatives thereof. In additional specific embodiments, the isolated nonprocessed PCSK9 comprises a mutation in one or more of the catalytic triad residues (D186, H226, S386). In other specific embodiments, the isolated nonprocessed, secreted PCSK9 is of SEQ ID NO: 34 (D186A) or of SEQ ID NO: 35 (S386A) or derivatives thereof. The present invention also encompasses methods employing nonprocessed, secreted PCSK9 for the evaluation of PCSK9 processing. One specific embodiment relates to a method for identifying an antagonist or agonist of PCSK9 processing comprising (a) providing nonprocessed, secreted PCSK9 to a well, plate, flask or appropriate environment containing a suitable reaction buffer (e.g., HEPES, TRIS, MOPS, NaCl, etc.; (b) contacting nonprocessed, secreted PCSK9 with a candidate antagonist or agonist; and (c) determining whether the nonprocessed, secreted PCSK9 is converted to processed, secreted PCSK9; wherein an increase in conversion of nonprocessed PCSK9 to processed PCSK9 indicates an agonist of PCSK9 processing and a decrease in conversion of nonprocessed PCSK9 to processed PCSK9 indicates an antagonist of PCSK9 processing.

Another embodiment of the present invention is a method for interfering with the processing of PCSK9 which comprises the administration of nucleic acid comprising a string of nucleotides encoding the pro domain of PCSK9, or a fragment thereof. In specific embodiments, the nucleic acid consists essentially of nucleic acid encoding the pro domain of PCSK9. The pro domain of PCSK9 corresponds roughly to amino acid residues 31 to 152 of human PCSK9, 35-155 of murine PCSK9 and 31-151 of rat PCSK9, or corresponding residues in PCSK9 of another species. Nucleic acid encoding the pro domain of PCSK9 suitable for use in the methods disclosed herein may be any nucleic acid encoding a pro domain of PCSK9, known mutants or equivalents thereof, or any protein with at least 80% homology to PCSK9 at the amino acid level having either conservative amino acid substitutions or modifications thereto; said protein which exhibits inhibition of PCSK9 processing. Nucleic acid encoding said protein should hybridize to the complement of nucleic acid encoding the pro domain of native PCSK9 (human, mouse, rat, or other species of PCSK9) under stringent hybridization conditions. In specific embodiments, the sequence encoding the pro domain is that encoding the pro domain of SEQ ID NO: 6, SEQ ID NO: 18 or SEQ ID NO: 19. In specific embodiments, the pro domain is the nucleic acid of SEQ ID NO: 33. In specific embodiments, the nucleic acid comprises SEQ ID NO: 33 or the corresponding sequence in mouse, rat or other PCSK9. In specific embodiments peptide fragments may be derived from the amino- or carboxy-termini of the pro domain.

Applicants have discovered that the pro domain of PCSK9 is an effective inhibitor of PCSK9 processing. Nucleic acid encoding the pro domain was administered and expressed in a cell and surprisingly found to be effective in inhibiting PCSK9 processing. Applicants, therefore, disclose herein methods for interfering with the processing of PCSK9 which comprise the delivery and expression of nucleic acid comprising a string of nucleotides encoding the pro domain of PCSK9 to cells, a cell population or subject of interest.

The nucleic acid may be administered in any manner capable of effectuating the delivery and expression of the nucleic acid in the cell, cell population or subject of interest including, but not limited to, the various delivery methods described above for administration of the PCSK9 expression constructs. As stated above, vectors of use in the methods of the present invention include, but are not limited to, plasmids and other expression constructs suitable for the expression of the desired PCSK9 protein at the appropriate level for the intended purpose.

In specific embodiments, the nucleic acids are introduced as part of a viral vector. Examples of specific viruses from which the vectors may be derived include lentiviruses, herpes viruses, adenoviruses, adeno-associated viruses, vaccinia virus, baculovirus, alphavirus, influenza virus, and other recombinant viruses with desirable cellular tropism.

Various companies produce viral vectors commercially, including, but by no means limited to, Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors).

Methods for constructing and using viral vectors are known in the art (see, e.g., Miller, et al, *BioTechniques* 7:980-990, 1992). In specific embodiments, the viral vectors are replication defective, that is, they are unable to replicate autonomously, and thus are not infectious, in the target cell. The replication defective virus may be a minimal virus, i.e., it retains only the sequences of its genome which are necessary for encapsidating the genome to produce viral particles. Defective viruses, which entirely or almost entirely lack viral genes, may also be used as well. Use of defective viral vectors allows for administration to cells in a specific, localized area, without concern that the vector can infect other cells. Thus, a specific tissue can be specifically targeted.

Examples of vectors comprising attenuated or defective DNA virus sequences include, but are not limited to, a defective herpes virus vector (Kanno et al, *Cancer Gen. Ther.* 6:147-154, 1999; Kaplitt et al, *J. Neurosci. Meth.* 71:125-132, 1997 and Kaplitt et al, *J. Neuro One.* 19:137-147, 1994).

Adenoviruses are eukaryotic DNA viruses that can be modified to efficiently deliver a nucleic acid of the invention to a variety of cell types. Attenuated adenovirus vectors, such as the vector described by Strafford-Perricaudet et al, *J. Clin. Invest.* 90:626-630, 1992, are desirable in some instances. Various replication defective adenovirus and minimum adenovirus vectors have been described (PCT Publication Nos. WO94/26914, WO94/28938, WO94/28152, WO94/12649, WO95/02697 and WO96/22378). The replication defective recombinant adenoviruses according to the invention can be prepared by any technique known to a person skilled in the art (Levrero et al, *Gene* 101:195, 1991; EP 185573; Graham, *EMBO J.* 3:2917, 1984; Graham et al, *J. Gen. Virol.* 36:59, 1977).

The adeno-associated viruses (AAV) are DNA viruses of relatively small size which can integrate, in a stable and site-specific manner, into the genome of the cells which they infect. They are able to infect a wide spectrum of cells without inducing any effects on cellular growth, morphology or differentiation, and they do not appear to be involved in human pathologies. The use of vectors derived from the AAVs for transferring nucleic acid in vitro and in vivo has been described (see Daly, et al, *Gene Ther.* 8:1343-1346, 2001; Larson et al, *Adv. Exp. Med. Bio.* 489:45-57, 2001; PCT Publication Nos. WO 91/18088 and WO 93/09239; U.S. Pat. Nos. 4,797,368 and 5,139,941 and EP 488528B1).

In another embodiment, the nucleic acid can be introduced in a retroviral vector, e.g., as described in U.S. Pat. Nos. 5,399,346, 4,650,764, 4,980,289, and 5,124,263; Mann et al, *Cell* 33:153, 1983; Markowitz et al, *J. Virol.*, 62:1120, 1988; EP 453242 and EP178220. Retroviruses are integrating viruses which infect dividing cells.

Lentiviral vectors can be used as agents for the direct delivery and sustained expression of nucleic acids in several tissue types, including brain, retina, muscle, liver and blood. The vectors can efficiently transduce dividing and nondividing cells in these tissues, and maintain long-term expression of the nucleic acid. For a review, see Zufferey et al, *J. Virol.* 72:9873-80, 1998 and Kafri et al, *Curr. Opin. Mol. Ther.* 3:316-326, 2001. Lentiviral packaging cell lines are available and known generally in the art. They facilitate the production of high-titer lentivirus vectors. An example is a tetracycline-inducible VSV-G pseudotyped lentivirus packaging cell line which can generate virus particles at titers greater than 106 IU/ml for at least 3 to 4 days; see Kafri et al, *J. Virol.* 73:576-584, 1999. The vector produced by the inducible cell line can be concentrated as needed for efficiently transducing nondividing cells in vitro and in vivo.

Sindbis virus is a member of the alphavirus genus and has been studied extensively since its discovery in various parts of the world beginning in 1953. Nucleic acid transduction based on alphavirus, particularly Sindbis virus, has been well-studied in vitro (see Straus et al, *Microbiol. Rev.,* 58:491-562, 1994; Bredenbeek et al, *J. Virol.,* 67:6439-6446, 1993; Ijima et al, *Int. J. Cancer* 80:110-118, 1999 and Sawai et al, *Biochim. Biophyr. Res. Comm.* 248:315-323, 1998. Many properties of alphavirus vectors make them a desirable alternative to other virus-derived vector systems being developed, including rapid engineering of expression constructs, production of high-titered stocks of infectious particles, infection of nondividing cells, and high levels of expression (Strauss et al, 1994 supra). Use of Sindbis virus for nucleic acid delivery has been described. Wahlfors et al, *Gene. Ther.* 7:472-480, 2000 and Lundstrom, *J. Recep. Sig. Transduct. Res.* 19(1-4):673-686, 1999.

In another embodiment, a vector can be introduced to cells by lipofection or with other transfection facilitating agents (peptides, polymers, etc.). Synthetic cationic lipids can be used to prepare liposomes for in vivo and in vitro transfection of nucleic acid (Feigner et al, *Proc. Natl. Acad. Sci. USA* 84:7413-7417, 1987 and Wang et al, *Proc. Natl. Acad. Sci. USA* 84:7851-7855, 1987). Useful lipid compounds and compositions for transfer of nucleic acids are described in PCT Publication Nos. WO 95/18863 and WO 96/17823, and in U.S. Pat. No. 5,459,127.

It is also possible to introduce the vector in vivo as a naked DNA plasmid. Naked DNA vectors can be introduced into desired host cells by methods known in the art, e.g., electroporation, microinjection, cell fusion, DEAE dextran, calcium phosphate precipitation, use of a gene gun, or use of a DNA vector transporter (see, e.g., Wilson, et al, *J. Biol. Chem.* 267:963-967, 1992; Williams et al, *Proc. Natl. Acad. Sci. USA* 88:2726-2730, 1991). Receptor-mediated DNA delivery approaches can also be used (Wu et al, *J. Biol. Chem.* 263: 14621-14624, 1988). U.S. Pat. Nos. 5,580,859 and 5,589,466 disclose delivery of exogenous DNA sequences, free of transfection facilitating agents, in a mammal. Recently, a relatively low voltage, high efficiency in vivo DNA transfer technique, termed electrotransfer, has been described (Vilquin et al, *Gene Ther.* 8:1097, 2001; Payen et al, *Exp. Hematol.* 29:295-300, 2001; Mir, *Bioelectrochemistry* 53:1-10, 2001; PCT Publication Nos. WO 99/01157, WO 99/01158 and WO 99/01175).

Standard recombinant DNA techniques for preparing and purifying DNA constructs may be used to prepare the nucleic acid described herein. Nucleic acid may be ligated into an expression vector which has been optimized for administration. Extraneous DNA may be at least partially removed, leaving essential elements such as a transcriptional promoter, transcriptional terminator, bacterial origin of replication and antibiotic resistance gene.

The present invention provides a pharmaceutically acceptable composition comprising the nucleic acid and a pharmaceutically acceptable carrier, excipient, diluent, stabilizer, buffer, or alternative designed to facilitate administration of the nucleic acid in the desired format and amount to the treated individual.

The amount of expressible nucleic acid to be introduced will depend on the strength of the transcriptional and translational promoters used in the nucleic acid construct.

Another embodiment of the present invention is a method for interfering with the processing of PCSK9 which comprises the administration of a polypeptide comprising sequence corresponding to the pro domain of PCSK9; or a fragment thereof. In specific embodiments, the polypeptide administered consists essentially of the pro domain of PCSK9 as described herein. The pro domain of PCSK9 corresponds roughly to amino acid residues 31 to 152 of human PCSK9, 32-155 of murine PCSK9, and 31-151 of rat PCSK9, or corresponding residues in PCSK9 of another species. In specific embodiments the polypeptide administered is the polypeptide of SEQ ID NO: 20. In specific embodiments, the polypeptide administered is a fragment of SEQ ID NO: 20.

Administration of nucleic acid or polypeptides in accordance with certain aspects of the present invention contemplates subcutaneous injection, intramuscular injection, intradermal introduction, impression through the skin, and other modes of administration such as intraperitoneal, intravenous, inhalation and oral delivery. In this case, it is desirable for the nucleic acid or polypeptide to be in a physiologically acceptable solution, such as, but not limited to, sterile saline or sterile buffered saline.

Determination of an effect on PCSK9 processing may, in specific embodiments, be determined in accordance with the methods described above for the selective recognition of processed, secreted PCSK9 to the exclusion of nonprocessed, secreted PCSK9. One skilled in the art may also determine an effect on processing by running a Western blot on the produced protein or a sample containing same, or by carrying out any alternative method suitable in the art for determining an effect on protein integrity. Alternatively, an effect on processing may be determined by carrying out a functional test, such as the DiI-LDL uptake assay described in Example 7 below. "Interfering" as used herein refers to the act of opposing, counteracting or curtailing the processing of PCSK9 as can be determined, for instance, as described above. It will, furthermore, be understood that such interference should effectuate a decrease in processing relative to that seen in the absence of the nucleic acid or polypeptide. Preferably, the nucleic acid or polypeptide interferes with processing of PCSK9 to such a degree that there is a decrease of at least 10%, of processing, and more preferably, a decrease of at least 20%, 30%, 40%, 50%, 60%, 70%, 80%, 90% and 95% of processing. Such inhibition/antagonism of PCSK9 processing is particularly effective in those instances where PCSK9 functioning is contributing at least in part to a particular phenotype, disease, disorder or condition which is negatively impacting the subject. Also contemplated are methods of using the disclosed nucleic acids or polypeptides in the manufacture of a medicament for treatment of a PCSK9-mediated disease, disorder or condition.

Methods of treatment in accordance with the present invention comprise administering to an individual a therapeutically effective amount of a nucleic acid molecule or polypeptide of the present invention. "Therapeutically effective" refers to the amount necessary at the intended dosage to achieve the desired therapeutic effect for the period of time desired. The desired effect may be, for example, amelioration of at least one symptom associated with PCSK9 function. A therapeutically effective amount will vary, as the skilled artisan will appreciate, according to various factors, including but not limited to the disease state, age, sex and weight of the individual, and the ability of the nucleic acid or polypeptide to elicit the desired effect in the individual. The response may be documented by in vitro assay, in vivo non-human animal studies, and/or further supported from clinical trials. The pharmaceutical composition of the present invention may be formulated by any number of strategies known in the art.

The following non-limiting Examples are presented to illustrate the present invention.

Example 1

Materials

A. PCSK9 Cloning

The PCSK9 gene was cloned from Human Fetal Liver Quick-Clone cDNA (BD BioScience). Pre PCSK9 forward and reverse primers were used to pre-amplify out the PCSK9 gene; Human Forward Pre PCSK9 primer 5' to 3' (DNA) GCA ACC TCT CCC CTG GCC CTC ATG (SEQ ID NO: 1); Human Reverse Pre PCSK9 primer 5' to 3' (DNA)-GCT TCC TGG CAC CTC CAC CTG GGG (SEQ ID NO: 2). The PCSK9 gene product was used as a template for Topo TA primers to generate the final PCSK9 sequence; Hum—For-PCSK9 Kozak primer 5' to 3' (DNA)—CCA CCA TGG GCA CCG TCA GCT CCA GG (SEQ ID NO: 3); TA-h Rev-PCSK9 (no stop) primer 5' to 3' (DNA)—CTG GAG CTC CTG GGA GGC CTG CGC CAG (SEQ ID NO: 4). The final PCSK9 insert was ligated into TOPO® TA vector using a pcDNA3.1/v5-His Topo® TA Expression kit (Invitrogen), followed by transformation into chemically competent TOP10 *E. coli* cells. Clones were selected and checked for correct insert by gel electrophoresis and sequenced. The following primers were used for generating mutations: plasmid pcDNA3.1-F1-S386A:F,5-CACAGAGTGGGACAGCA-CAGGCTGCTGCCCAC-3' (SEQ ID NO: 21) and R, 5-GTGGGCAGCAGCCTGTGCTGTCCCACTCGTG-3 (SEQ ID NO: 22). The resultant sequence encoding PCSK9 (SEQ ID NO: 5) within the TOPO® TA vector has an Isoleucine at 474 and a Glutamic Acid at position 670; FIG. 1. PCSK9 protein sequence (SEQ ID NO: 6) is illustrated in FIG. 2. For the D186A mutant used below, the following primers were used for generating the mutations: for plasmid pcDNA3.1-F1-D186A: F, 5'-GGAGGTGTATCTCCTAGC-CACCAGCATACAGAGTG-3' (SEQ ID NO: 23) and R, 5'-CACTCTGTATGCTGGTGGCTAGGAGATA-CACCTCC-3' (SEQ ID NO: 24). All PCSK9 constructs were expressed in a pcDNA3.1 backbone and selected with G418 (Invitrogen).

Figure 6:
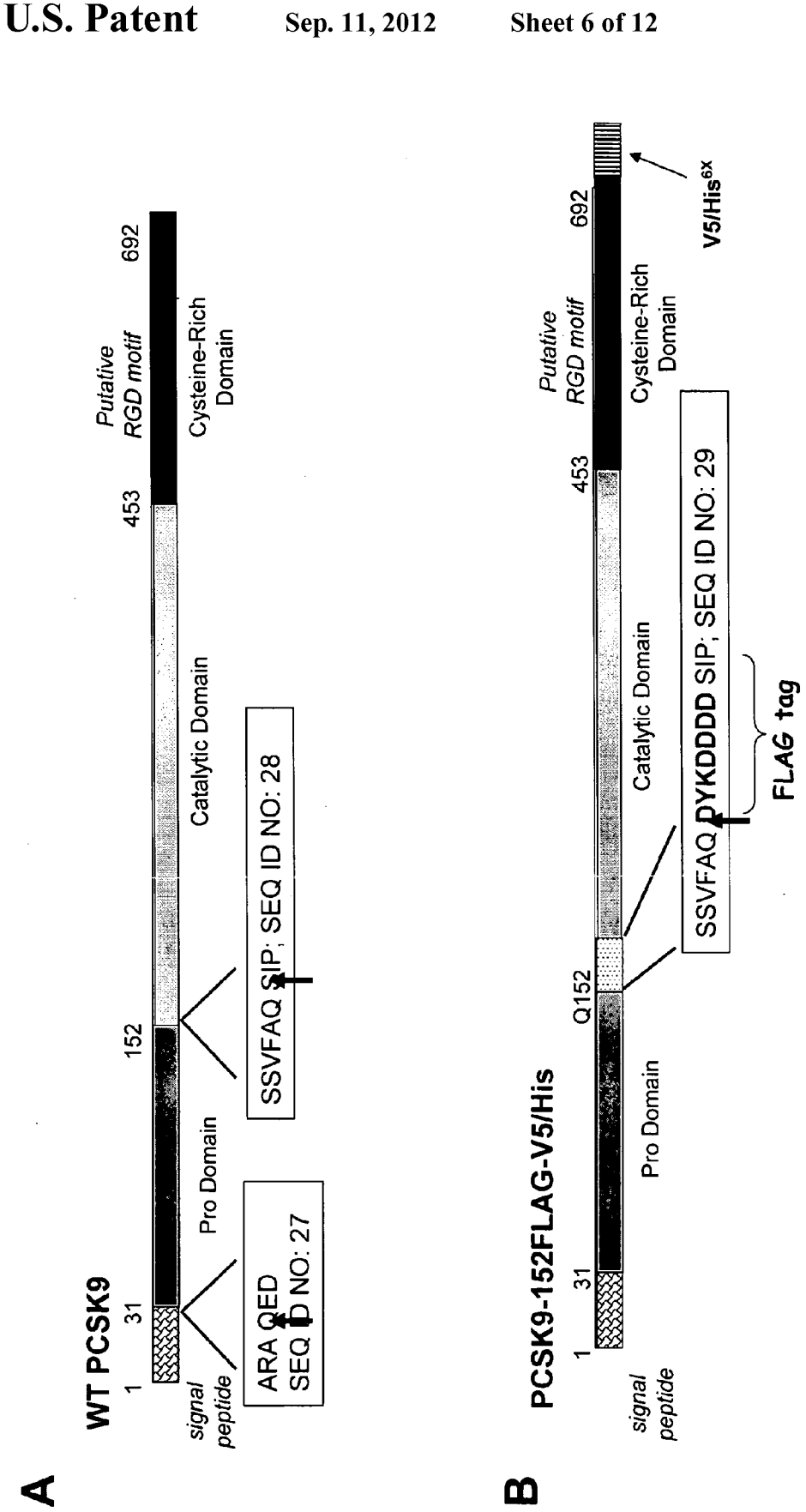
FIGS. 6A-6B illustrate, respectively, wild-type PCSK9, and a construct specifically designed for the identification and study of PCSK9 in the supernatant. Wild-type PCSK9 (FIG. 6A) contains a signal peptide (amino acids 1-30), a pro domain (amino acids 31-152), a catalytic domain (amino acids 153-453) and a C-term domain (amino acids 454-692). Both the site of cleavage by signal peptidase between A30 and Q31 and PCSK9 autoprocessing between Q152 and S153 are indicated. PCSK9-152FLAG-V5/His (FIG. 6B) was constructed to develop an assay to detect autoprocessed, secreted PCSK9 in cell media. PCSK9-152FLAG-V5/His contains a FLAG epitope (DYKDDDD; SEQ ID NO: 7) inserted between Q152 and S153 such that following autoprocessing of PCSK9, the portion of PCSK9 C-terminal to the autoprocessed site (the mature protein) will contain an N-terminal FLAG tag for detection. The PCSK9-152FLAG-V5/His construct contains a C-terminal V5 and His tag for detection.

As demonstrated in FIGS. 5A and 5B, Applicants ran a Western blot to analyze the media and cell lysate of cells transfected with wild-type PCSK9 and S386A PCSK9 mutant; see, e.g., Park et al., 2004 *J. Biol. Chem.* 279:50630-50638, for reference to S386A PCSK9 mutant. Quite unexpectedly, Applicants noted that S386A is released in the media in a nonprocessed form. This prompted the development of the following PCSK9 constructs and assays for employing them in the study of PCSK9 processing. The PCSK9 constructs developed as follows are depicted in FIGS. 6A-6B.

A FLAG epitope (DYKDDDD; SEQ ID NO: 7) was introduced between amino acids Q152 and S153 using the following primers: 5'-CTCCTCTGTCTTTGCCCAGGACTA-CAAAGACGATGACGATAGCATCCCGTGGAACCT GG-3' (SEQ ID NO: 9), and 5'-CCAGGTTCCACGGGAT-GCTATCGTCATCGTCTTTGTAGTC-CTGGGCAAAGACAGAGG AG-3' (SEQ ID NO: 10). The nucleotide sequence introduced to encode for the FLAG epitope was SEQ ID NO: 8. This generated PCSK9-152FLAG illustrated in FIG. 3; SEQ ID NO: 11. The PSCK9 ORF plus FLAG epitope were then cloned into pcDNA3.1 vector which has a V5/His at the C-terminus. This generated PCSK9-152FLAG-V5/His illustrated in FIG. 4; SEQ ID NO: 12.

PCSK9-152FLAG-V5/His with a S386A mutation was made by site-directed mutagenesis, replacing S386 with an alanine.

B. Generation of Cell Lines

HEK293 cells were plated at a density of $1.8 \times 10^6$ cells/6-well container in 1× Dulbecco's Modification of Eagle's Medium (DMEM) (Mediatech, Inc.) containing 100 units of penicillin and 100 μg/ml streptomycin sulfate and supplemented with 10% fetal bovine serum (FBS). The following day, plasmid DNA containing PCSK9-152FLAG, PCSK9-152FLAG-V5/His and PCSK9-152FLAG-V5/His-S386A was introduced into a HEK293T cell line using Fugene Transfection Reagent (Roche Diagnostics) according to the manufacturer's instructions. A ratio of reagent to plasmid DNA of 6:1 was used for transfections. To generate a control stable cell line, 6 μg of pcDNA3.1 was used to transfect HEK293 cells. HEK 293T PCSK9 stable cells were maintained in DMEM, 10% FBS-HI, 1×L-glutamine, 1 mg/ml G418 (Mediatech). Cells were adherent grown in T-175 flasks and split twice a week.

C. Western Blot Analysis

Cells carrying vector alone (pcDNA3.1) or vector plus PCSK9 (PCSK9-152 FLAG-V5/His and PCSK9-152 FLAG-V5/His-S386A) were plated in 1×DMEM containing 1 mg/ml G418 supplemented with 10% FBS. After 24 hr, the media was switched to DMEM media lacking serum. After an additional 6 hr, the media was removed and the cells were lysed in RIPA buffer (TEKNOVA) plus Complete protease inhibitor cocktail (Roche). Protein concentration was assayed with BCA Protein Assay Kit (Pierce). 1.7 mg of proteins from lysate or 15 μl media were loaded on 10-20% Tris-Glycine gels (Invitrogen). Following transfer, membranes were successively incubated with 1:5000 anti-VS (Invitrogen), 1:3000 anti-FLAG ml (Sigma-Aldrich Co.) or 1:3000 anti_FLAG m2 (Sigma-Aldrich Co.) primary antibody and 1:3000 anti-mouse IgG (H+L) alkaline phosphatase conjugate (Promega). Bands were subsequently detected using a 1-step NBT/BCIP Kit (Pierce) according to manufacturer's instructions.

Figure 7:
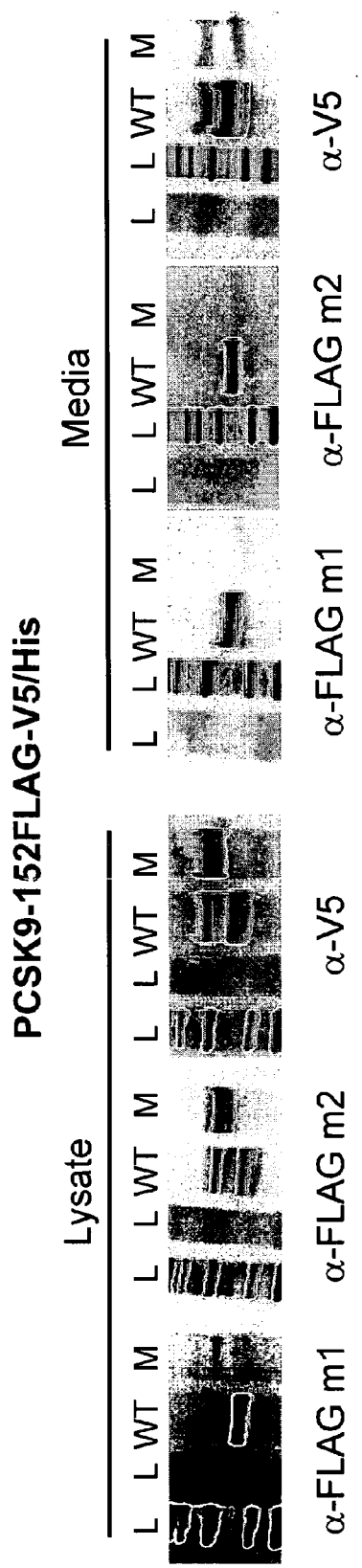
FIG. 7 illustrates the results of western blot analysis with the PCSK9-152FLAG-V5/His cell line. Both intracellular (Lysate) and secreted (Media) PCSK9 was detected in the stable cell line expressing PCSK9-152FLAG-V5/His proteins. Western blot analysis was performed using three separate antibodies, including: anti-FLAG m1, which recognizes the FLAG tag only when present at the N-terminus of the protein, anti-FLAG m2, which recognizes the FLAG epitope regardless of its position within the protein and anti-V5, which recognizes the V5 epitope present at the C-terminus of the PCSK9-152FLAG-V5/His protein. The lanes in the blot analysis are as follows: (L) Ladder; (WT) Wt PCSK9; and (M) S386A PCSK9.

FIG. 7 illustrates the results of a Western blot analysis using the PCSK9-152 FLAG-V5/His and PCSK9-152 FLAG-V5/His-S386A cell lines. Both intracellular (Lysate) and secreted (Media) PCSK9 was detected in stable cell lines expressing PCSK9-152 FLAG-V5/His proteins.

D. Labeling of anti-FLAG m1 Antibody with $Eu^{+3}$

M1 monoclonal antibody (Sigma-Aldrich Co.) at 4.5 mg/mL (147 μL, 661 μg, 4.13 nmol) was dialyzed against labeling buffer 100 mM NaHCO$_3$, 200 mM NaCl, pH 8.6 (2×90 min, 100 mL). 50 μL (70 nmol, 17 equiv.) of a 1.4 mM stock of Eu(W1024)-ITC (Perkin-Elmer) in H$_2$O was added to the dialyzed material. The material was incubated for 3 hours at 30° C., and unreacted ITC chelate was then scavenged by addition of 300 μL of 1M Tris, pH 9.0 for 30 minutes. The quenched material was passaged over a Nap-5 column (GE Healthcare) which had been preequilibrated in 50 mM potassium phosphate, 350 mM NaCl, 10% (v/v) glycerol, pH 7.0. The material was eluted in the same in a total volume of 1 mL and 5% BSA added to a final concentration of 0.05% (w/v) BSA. An 80% recovery (530 mg, 3.3 nmol) was assumed giving a 3.3 μM stock of labeled antibody.

Antibody was characterized by diluting to 1 nM in the same buffer and then reading 5×100 μl, wells of a black 96 well U bottom plate (Dynatech) on a Discovery instrument (Packard) to give an average of 452,000 B counts/nM/100 μL.

E. Plasmid pcDNA3.1-HA-Pro Construction

Nucleic acid encoding the human PCSK9 pro domain (SEQ ID NO: 20) was manipulated to contain an HA epitope with additional amino acids (SEQ ID NO: 13). Starting with plasmid DNA pcDNA3.1-F1-V5-His, primers ccgggGCG-GCCGCATGGGCACCGTCAGCTCCAGGCGG (SEQ ID NO: 14) and ccgggTCTAGActgggcaaagacagaggag (SEQ ID NO: 15) were used to amplify, through PCR, the insert DNA which was subcloned into pcDNA3.1/+ at NotI/XbaI. An HA epitope was added through mutagenesis reaction by using primers CCCGCGGGCGCCCGTGCGCAGGAGTAC-CCTTATGATGTTCCTGATTATGCCCAGGAG GAC-GAGGACGG (SEQ ID NO: 16) and CCGTCCTCGTCCTC-CTGGGCATAATCAGGAACATCATAAGGGTACTCCTG CGCACGG GCGCCCGCGGG (SEQ ID NO: 17). The clone was confirmed through full length sequencing. The insert nucleic acid sequence is SEQ ID NO: 25 and the translation of pcDNA3.1-HA-Pro is found in SEQ ID NO: 26.

Example 2

Figure 8:
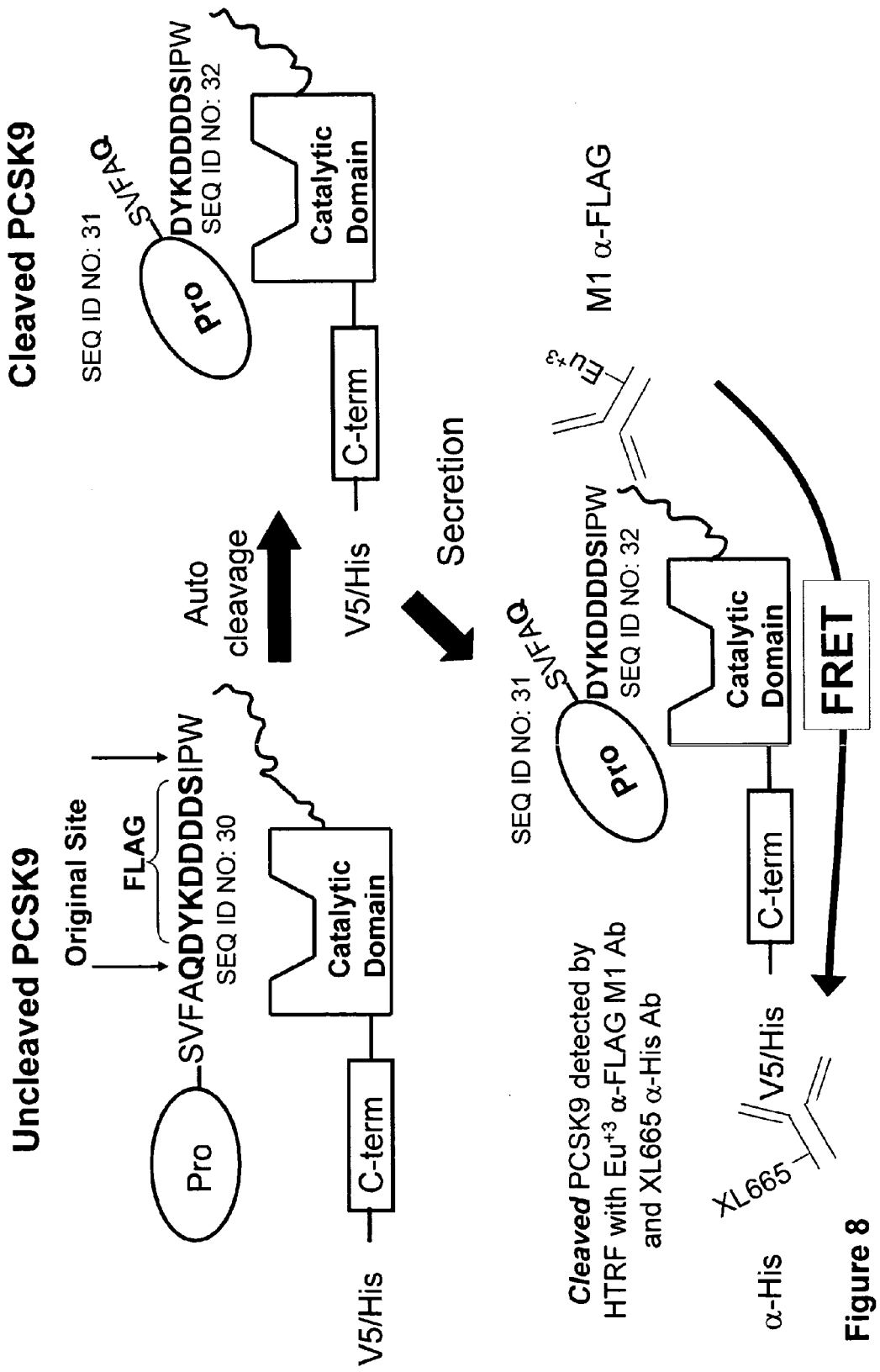
FIG. 8 illustrates the TR-FRET-based appearance assay to detect autoprocessed, secreted PCSK9-152FLAG-V5/His protein. Following autoprocessing, the PCSK9-152FLAG-V5/His protein is secreted from cells. Following secretion, media is combined with FRET reagents, and autoprocessed PCSK9 is detected using $Eu^{+3}$-labeled anti-FLAG M1 antibody and XL665-labeled anti-His antibody.

PCSK9-152FLAG-V5/His APPEARANCE
Time-Resolved Fluorescence Energy Transfer
("TR-FRET") Assay The following TR-FRET-based appearance assay depicted in FIG. 8 was developed by Applicants to detect autoprocessed, secreted PCSK9-152 FLAG-V5/His protein.

PCSK9-152FLAG-V5/His and PCSK9-152FLAG-V5/His-S386A cells were dissociated from the T-175 flask using Cell Stripper solution (Mediatech), counted and plated at a cell density of $1 \times 10^6$ cells per ml. A range of cells (1562-50,000) per well were provided in a 96 well plate with 50 μl of Phenol Red Free DMEM, 2% FBS-HI, 1×L-glutamine, and 1 mg/ml G418 (Mediatech). Plates were incubated at 37° C., 5% CO2 for 16 hours. Media was removed and combined with 50 μl of 2×TR-FRET Assay Buffer in 96 well black plates (Packard). This 2× buffer consisted of 100 mM Hepes pH 6.5, 100 mM NaCl, 0.1% BSA, 2 mM CaCl$_2$, 100 μM $Eu^{+3}$ anti-FLAG m1 antibody and 2.6 nM XL665-labeled anti-His antibody (Cis BioInternational). The plates were then incubated at room temperature for 6 hours. The plates were read on a Discovery Microplate Analyzer (Packard), a time-resolved fluorescence detector. Data are reported as the fluorescence at 665 nm (XL665, A counts), the fluorescence at 620 nm ($Eu^{+3}$, B counts) and their ratio multiplied by 10,000.

Figure 9:
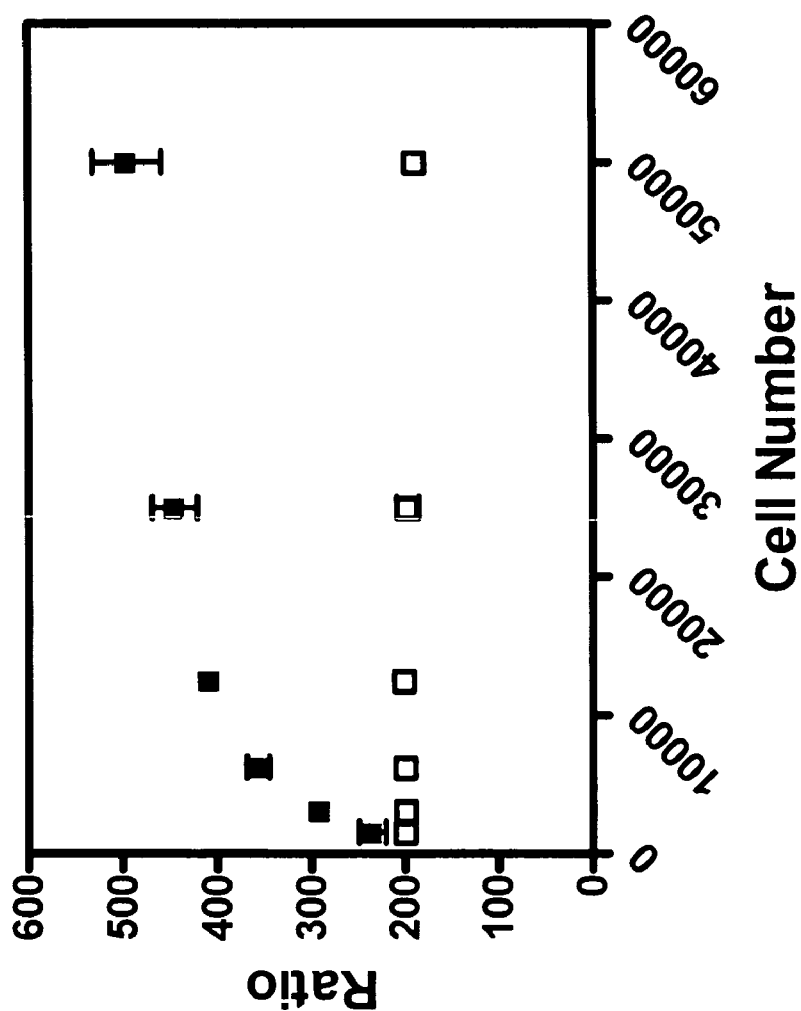
FIG. 9 illustrates the results from TR-FRET experiments of PCSK9-152FLAG-V5/His and PCSK9-152FLAG-V5/His-S386A cell lines. Increasing numbers of cells were plated and allowed to grow overnight at 37° C. The following morning, media containing secreted PCSK9 was combined with reaction buffer containing $Eu^{+3}$-labeled anti-FLAG M1 antibody and XL665-labeled anti-His antibody to measure secretion of processed PCSK9. The ratio of fluorescence at 620 and 665 nm was determined using a Discovery plate reader. Results from PCSK9-152FLAG-V5/His cells (closed squares) and PCSK9-152FLAG-V5/His-S386A cells (open squares) are indicated.

FIG. 9 illustrates the results from TR-FRET experiments of PCSK9-152 FLAG-V5/His and PCSK9-152 FLAG-V5/His-S386A cell lines.

As indicated, autoprocessed, secreted PCSK9 was detected in media from cells expressing PCSK9-152FLAG-V5/His, but not from cells expressing PCSK9-152FLAG—V5/His-S386A. Under these experimental conditions, the window between the ratio observed with PCSK9-152FLAG-V5/His and PCSK9-152FLAG-V5/His-S386A at a cell density of 50,000 cells per well was approximately 3-fold. The ratio observed with PCSK9-152FLAG-V5/His-S386A did not change when cell number was titrated upward, indicating that nonprocessed PCSK9-152FLAG-V5/His-S386A is not detected.

Example 3

PCSK9 Appearance Assay for Antagonists/Agonists of PCSK9 Processing

The above findings support the use of such an assay for the evaluation of PCSK9 processing. The concept of identifying secreted PCSK9 with a specific N-terminal epitope exposed only upon processing is useful for the identification and evaluation of inhibitors/activators of PCSK9 processing.

Example 4

Inhibition of PCSK9 Processing by Pro Domain

Figure 10:
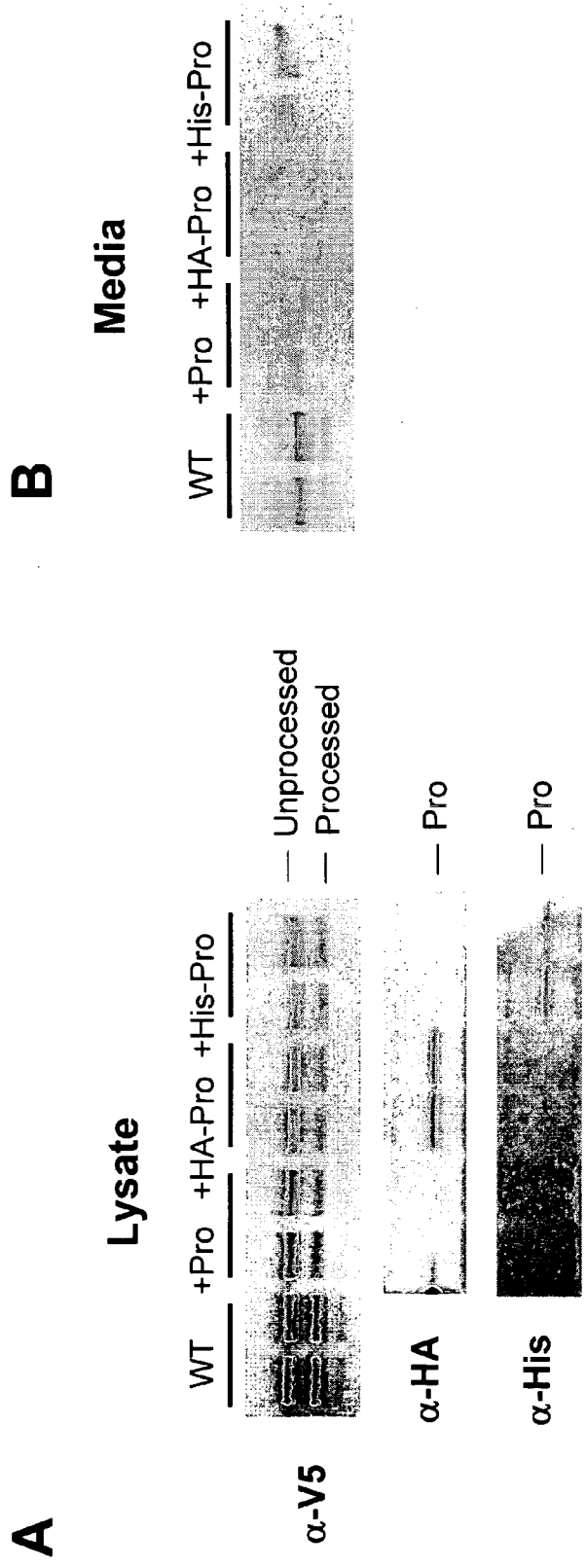
FIGS. 10A and 10B illustrate inhibition of PSCK9 processing through co-transfection of PCSK9 pro domain. The figure illustrates the inhibition of PCSK9 processing is similar whether the domain is untagged, or tagged at the N-terminus with either an HA or His tag. The blots on the bottom of FIG. 10A show that the His and HA Pro domains are expressed. The lanes are in order wild-type; wild-type; pro domain; HA pro domain; His pro domain.

As stated prior, transfection of V5/His-tagged WT PCSK9 results in detection of both processed and nonprocessed protein detected in the cell lysate, whereas only processed PCSK9 is detected in the media; also see FIGS. 10A and 10B. Of note, there is more processed versus nonprocessed PCSK9 detected.

To determine whether the processing of PCSK9 is inhibited by overexpression of its pro domain in cell culture, co-transfection of an untagged, HA-tagged or His-tagged PCSK9 pro domain with wild type V5/His-tagged PCSK9 was carried out. As shown in FIG. 10A, both HA- and His-tagged pro domain is detected in cell lysate and, importantly, the amount of processed PCSK9 is reduced compared to cells expressing wild type alone; see, FIG. 10A. In agreement with an inhibitory role of PCSK9's pro domain on processing, less processed PCSK9 was detected in the media from cells in which the pro domain was co-transfected; see FIG. 10B. The fact that processing of WT PCSK9 was similar in cotransfections with either untagged or tagged pro domain indicate that the tags do not affect pro domain inhibition of processing.

Example 5

Purification of PCSK9

Media generated from one cell factory was stored in a 1 L PEG bottle at 4° C. TALON immobilized metal affinity chromatography (IMAC) resin (10 ml, Clontech), was added and rocked at room temperature for one hour on an Adams Nutator. Resin was collected by gravity filtration and bulk washed according to reagent instructions. Less than 10 mg of eluted protein, concentrations determined by A280 nm using a Nanoprop ND-1000 spectrophotometer, was loaded onto a Superdex 200 10/300 GL size exclusion column (GE Healthcare) run in a 25 mM HEPES, 30 mM NaCl, 0.1 mM $CaCl_2$ and 5% glycerol buffer at pH 7.90 (buffer A). Peak fractions were loaded onto a 6 ml RESOURCE Q column (GE Healthcare). A 6.0 ml/minute linear gradient of 0-50% elution buffer A plus 1.0M NaCl (buffer B) in a volume of 120 ml was used. Peak fractions were concentrated using a Centricon Centriplus-5 concentrator (Millipore) to concentrations of greater than 1 mg/ml and stored at −20° C.

This method was used to isolate secreted, processed PCSK9 and secreted, nonprocessed PCSK9.

Example 6

Preparation OF LDL AND diI-LDL

Blood for LDL isolation was obtained from healthy human volunteers. Blood (200 ml) was collected in EDTA tubes and spun at 15,000 rpm for 15 min at 4° C. Plasma density was adjusted to 1.02 g/ml with sodium bromide and the tubes were centrifuged at 45,000 rpm in Ti70 ultracentrifuge rotor for 20 hr. The VLDL layer was removed and the bottom layer was recalibrated to a density of 1.063 g/ml with sodium bromide. The tubes were again centrifuged at 45,000 rpm in Ti70 rotor for 72 hr. The LDL layer was removed and dialysed against PBS pH 7.4 and 0.5 M EDTA. The final protein concentration was determined using a BCA Protein Assay Kit. LDL was labeled with a fluorescent DiI particle (Molecular Probes). A stock solution containing 3 mg of DiI dissolved in 1 ml of dimethyl sulfoxide (DMSO) was prepared. This stock solution of DiI was added to LDL at a final concentration of 135 μg of DiI to 1 ml of LDL. The labeling reaction was incubated at 37° C. for 24 hr in the dark followed by LDL isolation as mentioned above.

Example 7

DiI-LDL Uptake Assay

HEK293 cells stably expressing the vector pcDNA3.1 alone were plated in a 96-well poly D-lysine coated plate (Corning) at a density of 30,000 cells/well in 1×DMEM, containing 1 mg/ml G418 and 10% FBS (HEK293). A similar plating protocol was followed for HepG2 and CHO cells except that G418 was not added to the media. After 24 hr, the media was switched to DMEM media lacking serum. After 18 hr, the media was removed and the cells were washed with OptiMEM (Invitrogen). Purified PCSK9 protein was added to the cells in 100 μl of mixture B (DMEM containing 10% lipoprotein deficient serum (LPDS) (Intracel) and 10 μg/ml dI-LDL). To measure non-specific binding, 100 μl of mixture B that also contained 400 μg/ml unlabeled LDL was added to control wells. The plates were incubated at 37° C. for 6.5 hours and the cells were washed quickly in Tris-buffered saline (TBS, Biorad) containing 2 mg/ml Bovine Serum Albumin (BSA) (Sigma). The wash step was repeated, but this time the wash buffer was incubated for 2 min with the cells. Last, the cells were quickly washed twice with TBS (without BSA) and lysed in 100 μl RIPA buffer. The lysate was transferred to a 96-well black plate (Thermo Labsystem) and fluorescence was measured using a SpectraMAX tunable spectrofluorometer (Molecular Devices) at an excitation wavelength of 520 nm and an emission wavelength of 580 mm Total cellular protein was measured in each well using a BCA Protein Assay and the fluorescence units were normalized to total protein. The amount of specific LDL uptake (specific counts) is the difference between the total counts measured (in the absence of unlabeled LDL) and the counts measured in the presence of an excess of unlabeled LDL (non-specific background fluorescence). The amount of PCSK9 protein required for 50% inhibition of diI-LDL uptake ($EC_{50}$) was determined by fitting data to a sigmoidal dose response curve using nonlinear regression (GraphPad Software Inc.).

Example 8

Figure 11:
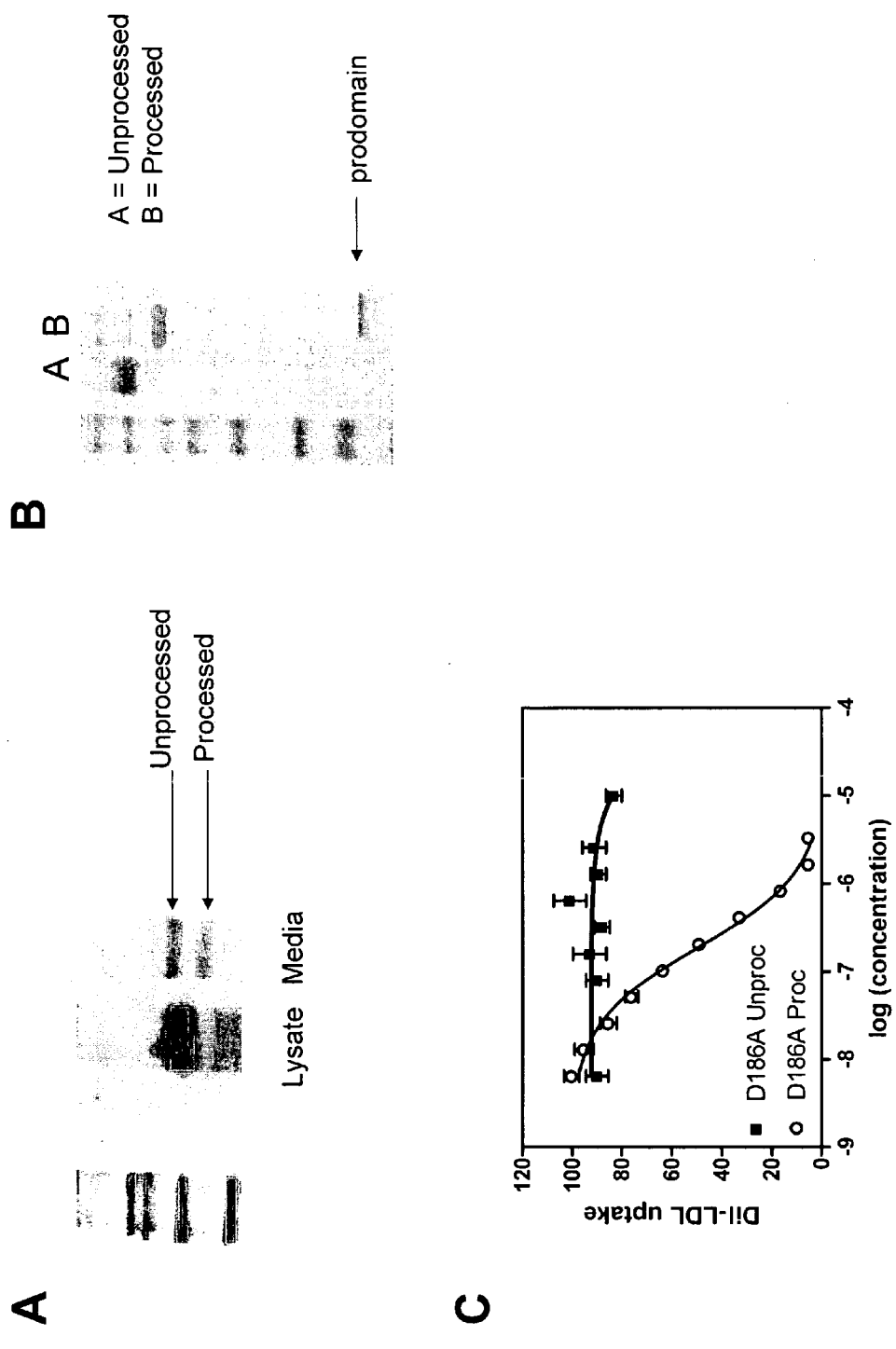
FIGS. 11A-11C illustrate, respectively, (i) a PCSK9 Western Blot showing the relative processing observed in HEK293 cells expressing catalytic mutant D186A; (ii) a Coomassie stained gel of highly purified processed and nonprocessed D186A mutant; and (ii) the activity of processed and nonprocessed forms of PCSK9 mutant D186A in a PCSK9-dependent LDL-uptake assay.

PCSK9 Processing, but not an Intact Catalytic Triad, is Required for PCSK9's Effects on Cellular LDL Uptake and Interaction with LDLR PCSK9 processing has been shown to require residues D186, H226, and S386, which constitute the internal serine protease-like catalytic triad; see Seidah et al., 2003 *PNAS* 100:928-933; and Naureckiene et al., 2003 *Archives Biochem. Biophys.* 420:55-67. A Western blot analyses of HEK293 cells that stably express the PCSK9 single mutant D186A show that the D186A PCSK9 mutant is processed to a small extent (10-20%) and is secreted both as the pro form (~78 kD) and the processed form (~64 kD) (FIG. 11A). Media from the D186A stable cell line was purified using column chromatography (as described) to obtain both purified nonprocessed and processed D186A (FIG. 11B). Similar to the WT PCSK9 protein processed D186A retains the pro domain after several column purifications (FIG. 11B).

The purified processed and nonprocessed forms of D186A were tested in the PCSK9-dependent LDL-uptake assay (FIG. 11C). While the nonprocessed form of D186A is only weakly active, the processed form is active with an $EC_{50}$ of 189 nM, approximately 4-fold weaker in potency than WT PCSK9 in HEK293 cells. Importantly, this data demonstrates that the processing of PCSK9 is required for its functional activity on LDL-uptake.

Example 9

Processing of Nonprocessed PCSK9 after Secretion into the Media

Figure 12:
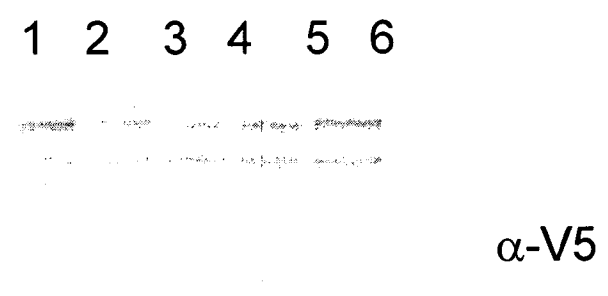

PCSK9 secretion from transfected cells was allowed for 2 hours. The media was then removed from cells and incubated at 37 degrees for the following periods: 2 hours, 6 hours, 18 hours, 42 hours, 66 hours. FIG. 12 illustrates a western blot (anti-V5) looking at secreted D186A protein after secretion into media. PCSK9 secretion was allowed for 2 hours, at which point the media was removed from cells and incubated at 37 degrees for the above-indicated periods of time. As shown in FIG. 12, the ratio of unprocessed: processed D186A changes over time, with less unprocessed and more processed protein accumulating, indicating that D186A processing occurs.

What is claimed:

1. A method for identifying processed, secreted proprotein convertase subtilisin-kexin type 9 ("PCSK9") to the exclusion of nonprocessed, secreted PCSK9 in cell supernatant, which comprises:

(a) transforming cells with an expression construct comprising nucleic acid encoding PCSK9 wherein an epitope tag is inserted immediately subsequent to nucleic acid encoding residue Q in the stretch of amino acids FAQ, said stretch of amino acids corresponding to amino acid residues 150-152 in human PCSK9, amino acid residues 153-155 in murine PCSK9, or amino acid residues 149-151 in rat PCSK9;

(b) introducing into the supernatant of said transforming cell an antibody or anti-epitope molecule capable of recognizing the epitope tag only when located at the extreme amino-terminus, said antibody or anti-epitope molecule carrying a selectable marker which can be detected; and (c) detecting bound antibody or anti-epitope molecule carrying said selectable marker, bound antibody or anti-epitope molecule indicating processed, secreted PCSK9.

2. The method of claim 1 wherein the cells are HEK 293 cells.

3. The method of claim 1 wherein the cells are HEPG2 cells.

4. The method of claim 1 wherein the epitope tag of claim 1 is a tag comprising SEQ ID NO: 7.

5. The method of claim 1 wherein the epitope tag is inserted into a sequence selected from the group consisting of: a nucleic acid encoding the amino acid sequence set forth in SEQ ID NO: 6, a nucleic acid encoding the amino acid sequence set forth in SEQ ID NO: 18, a nucleic acid encoding the amino acid sequence set forth in SEQ ID NO: 19, a nucleic acid encoding the amino acid sequence set forth in SEQ ID NO: 34, and a nucleic acid encoding the amino acid sequence set forth in SEQ ID NO: 35.

6. The method of claim 4 wherein the antibody or anti-epitope molecule of step (b) is an antibody that binds specifically to the tag.

7. The method of claim 1 wherein the selectable marker of step (b) is $Eu^{3+}$.

8. The method of claim 1 which further comprises:

(a) inserting an additional epitope tag in the PCSK9 sequence; wherein said additional epitope tag is inserted in the signal peptide region or subsequent to amino acid residue S corresponding to S 153 in human PCSK9; S 156 in murine PCSK9; or S 152 in rat PCSK9;

(b) introducing into cell supernatant an additional antibody or anti-epitope molecule capable of recognizing the additional epitope tag; said antibody or anti-epitope molecule bearing a selectable marker which can be independently detected; and (c) detecting bound antibody or anti-epitope molecule carrying the selectable marker, bound antibody or anti-epitope molecule indicating total processed and nonprocessed PCSK9.

9. The method of claim 8 wherein the additional epitope tag is inserted into the signal peptide region.

10. The method of claim 8 wherein the additional epitope tag is inserted at the C-terminus.

11. The method of claim 8 wherein the additional epitope tag is a V5/His6X tag.

12. The method of claim 11 wherein the additional antibody or anti-epitope molecule to detect the additional epitope tag is anti-His6X antibody.

13. The method of claim 12 wherein the additional antibody or anti-epitope molecule to detect the additional epitope tag is XL665-labeled anti-His6X antibody.

14. The method of claim 8 wherein the antibody or anti-epitope molecule and additional antibody or anti-epitope molecule have fluorophores as their selectable markers and detection of bound antibody or anti-epitope molecule is through detection of fluorescence resonance energy transfer between the fluorophores on the antibody or anti-epitope molecules.

15. A method for identifying processed, secreted proprotein convertase subtilisin-kexin type 9 ("PCSK9") to the exclusion of nonprocessed, secreted PCSK9 in cell supernatant, which comprises:

(a) collecting cell supernatant from an individual cell transfected with an expression construct comprising nucleic acid encoding PCSK9 wherein an epitope tag is inserted immediately subsequent to nucleic acid encoding residue Q in the stretch of amino acids FAQ, said series of amino acids corresponding to amino acid residues 150-152 in human PCSK9, amino acid residues 153-155 in murine PCSK9, or amino acid residues 149-151 in rat PCSK9;

(b) introducing into the cell supernatant an antibody or anti-epitope molecule capable of recognizing the epitope tag only when located at the extreme amino-terminus, said antibody or anti-epitope molecule carrying a selectable marker which can be detected; and (c) detecting bound antibody or anti-epitope molecule carrying said selectable marker, bound antibody or anti-epitope molecule indicating processed, secreted PCSK9.

* * * * *

SEQUENCE LISTING

```
<160> NUMBER OF SEQ ID NOS: 36

<210> SEQ ID NO 1
<211> LENGTH: 24
<212> TYPE: DNA
<213> ORGANISM: Artificial Sequence
<220> FEATURE:
<223> OTHER INFORMATION: PCR primer

<400> SEQUENCE: 1
gcaacctctc ccctggccct catg                                          24

<210> SEQ ID NO 2
<211> LENGTH: 24
<212> TYPE: DNA
<213> ORGANISM: Artificial Sequence
<220> FEATURE:
<223> OTHER INFORMATION: PCR primer

<400> SEQUENCE: 2
gcttcctggc acctccacct gggg                                          24

<210> SEQ ID NO 3
<211> LENGTH: 26
<212> TYPE: DNA
<213> ORGANISM: Artificial Sequence
<220> FEATURE:
<223> OTHER INFORMATION: PCR primer

<400> SEQUENCE: 3
ccaccatggg caccgtcagc tccagg                                        26

<210> SEQ ID NO 4
<211> LENGTH: 27
<212> TYPE: DNA
<213> ORGANISM: Artificial Sequence
<220> FEATURE:
<223> OTHER INFORMATION: PCR primer

<400> SEQUENCE: 4
```

```
ctggagctcc tgggaggcct gcgccag                                          27
```

<210> SEQ ID NO 5
<211> LENGTH: 2076
<212> TYPE: DNA
<213> ORGANISM: homo sapiens

<400> SEQUENCE: 5

```
atgggcaccg tcagctccag gcggtcctgg tggccgctgc cactgctgct gctgctgctg     60
ctgctcctgg gtcccgcggg cgcccgtgcg caggaggacg aggacggcga ctacgaggag    120
ctggtgctag ccttgcgttc cgaggaggac ggcctggccg aagcacccga gcacggaacc    180
acagccacct tccaccgctg cgccaaggat ccgtggaggt tgcctggcac ctacgtggtg    240
gtgctgaagg aggagaccca cctctcgcag tcagagcgca ctgcccgccg cctgcaggcc    300
caggctgccc gccggggata cctcaccaag atcctgcatg tcttccatgg ccttcttcct    360
ggcttcctgg tgaagatgag tggcgacctg ctggagctgg ccttgaagtt gccccatgtc    420
gactacatcg aggaggactc ctctgtcttt gcccagagca tcccgtggaa cctggagcgg    480
attcccctc acggtaccg gcggatgaa taccagcccc cgacggagg cagcctggtg        540
gaggtgtatc tcctagacac cagcatacag agtgaccacc gggaaatcga gggcagggtc    600
atggtcaccg acttcgagaa tgtgcccgag gaggacggga cccgcttcca cagacaggcc    660
agcaagtgtg acagtcatgg cacccacctg gcaggggtgg tcagcggccg ggatgccggc    720
gtggccaagg gtgccagcat gcgcagcctg cgcgtgctca actgccaagg gaagggcacg    780
gttagcggca ccctcatagg cctggagttt attcggaaaa gccagctggt ccagcctgtg    840
gggccactgg tggtgctgct gcccctggcg ggtgggtaca gccgcgtcct caacgccgcc    900
tgccagcgcc tggcgagggc tggggtcgtg ctggtcaccg ctgccggcaa cttccgggac    960
gatgcctgcc tctactcccc agcctcagct cccgaggtca tcacagttgg ggccaccaat   1020
gcccaggacc agccggtgac cctggggact ttggggacca cttttggccg ctgtgtggac   1080
ctctttgccc caggggagga catcattggt gcctccagcg actgcagcac ctgctttgtg   1140
tcacagagtg gacatcaca ggctgctgcc cacgtggctg gcattgcagc catgatgctg   1200
tctgccgagc cggagctcac cctggccgag ttgaggcaga gactgatcca cttctctgcc   1260
aaagatgtca tcaatgaggc ctggttccct gaggaccagc gggtactgac ccccaacctg   1320
gtggccgccc tgcccccag cacccatggg gcaggttggc agctgttttg caggactgtg   1380
tggtcagcac actcggggcc tacacggatg ccacagcca tcgcccgctg cgccccagat   1440
gaggagctgc tgagctgctc cagtttctcc aggagtggga gcggcgggg cgagcgcatg   1500
gaggcccaag gggcaagct ggtctgccgg gcccacaacg cttttggggg tgagggtgtc   1560
tacgccattg ccaggtgctg cctgctaccc caggccaact gcagcgtcca cacagctcca   1620
ccagctgagg ccagcatggg gacccgtgtc cactgccacc aacagggcca cgtcctcaca   1680
ggctgcagct cccactggga ggtggaggac cttggcaccc acaagccgcc tgtgctgagg   1740
ccacgaggtc agcccaacca gtgcgtgggc cacaggagg ccagcatcca cgcttcctgc   1800
tgccatgccc caggtctgga atgcaaagtc aaggagcatg gaatcccggc ccctcaggag   1860
caggtgaccg tggcctgcga ggagggctgg acccctgactg gctgcagtgc cctccctggg   1920
acctcccacg tcctggggc ctacgccgta gacaacacgt gtgtagtcag gagccgggac   1980
gtcagcacta caggcagcac cagcgaagag gccgtgacag ccgttgccat ctgctgccgg   2040
agccggcacc tggcgcaggc ctcccaggag ctccag                              2076
```

<210> SEQ ID NO 6
<211> LENGTH: 692
<212> TYPE: PRT
<213> ORGANISM: homo sapiens

<400> SEQUENCE: 6

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
    370                 375                 380

```
Thr Ser Gln Ala Ala His Val Ala Gly Ile Ala Met Met Leu
385                 390                 395                 400

Ser Ala Glu Pro Glu Leu Thr Leu Ala Glu Leu Arg Gln Arg Leu Ile
            405                 410                 415

His Phe Ser Ala Lys Asp Val Ile Asn Glu Ala Trp Phe Pro Glu Asp
        420                 425                 430

Gln Arg Val Leu Thr Pro Asn Leu Val Ala Ala Leu Pro Pro Ser Thr
            435                 440                 445

His Gly Ala Gly Trp Gln Leu Phe Cys Arg Thr Val Trp Ser Ala His
    450                 455                 460

Ser Gly Pro Thr Arg Met Ala Thr Ala Ile Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
    530                 535                 540

Ser Met Gly Thr Arg Val His Cys His Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Glu Ala Val
            660                 665                 670

Thr Ala Val Ala Ile Cys Cys Arg Ser Arg His Leu Ala Gln Ala Ser
        675                 680                 685

Gln Glu Leu Gln
    690

<210> SEQ ID NO 7
<211> LENGTH: 7
<212> TYPE: PRT
<213> ORGANISM: Artificial Sequence
<220> FEATURE:
<223> OTHER INFORMATION: Flag Epitope

<400> SEQUENCE: 7

Asp Tyr Lys Asp Asp Asp Asp
 1               5

<210> SEQ ID NO 8
<211> LENGTH: 21
<212> TYPE: DNA
<213> ORGANISM: Artificial Sequence
<220> FEATURE:
<223> OTHER INFORMATION: Flag Epitope
```

<400> SEQUENCE: 8
gactacaaag acgatgacga t    21

<210> SEQ ID NO 9
<211> LENGTH: 59
<212> TYPE: DNA
<213> ORGANISM: Artificial Sequence
<220> FEATURE:
<223> OTHER INFORMATION: PCR primer

<400> SEQUENCE: 9
ctcctctgtc tttgcccagg actacaaaga cgatgacgat agcatcccgt ggaacctgg    59

<210> SEQ ID NO 10
<211> LENGTH: 59
<212> TYPE: DNA
<213> ORGANISM: Artificial Sequence
<220> FEATURE:
<223> OTHER INFORMATION: PCR primer

<400> SEQUENCE: 10
ccaggttcca cgggatgcta tcgtcatcgt ctttgtagtc ctgggcaaag acagaggag    59

<210> SEQ ID NO 11
<211> LENGTH: 699
<212> TYPE: PRT
<213> ORGANISM: Artificial Sequence
<220> FEATURE:
<223> OTHER INFORMATION: PCSK9-152Flag

<400> SEQUENCE: 11

```
Met Gly Thr Val Ser Ser Arg Arg Ser Trp Trp Pro Leu Pro Leu Leu
 1               5                  10                  15

Leu Leu Leu Leu Leu Leu Leu Gly Pro Ala Gly Ala Arg Ala Gln Glu
             20                  25                  30

Asp Glu Asp Gly Asp Tyr Glu Glu Leu Val Leu Ala Leu Arg Ser Glu
         35                  40                  45

Glu Asp Gly Leu Ala Glu Ala Pro Glu His Gly Thr Thr Ala Thr Phe
     50                  55                  60

His Arg Cys Ala Lys Asp Pro Trp Arg Leu Pro Gly Thr Tyr Val Val
 65                  70                  75                  80

Val Leu Lys Glu Glu Thr His Leu Ser Gln Ser Glu Arg Thr Ala Arg
                 85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Asp Tyr Lys Asp Asp Asp Asp Ser
145                 150                 155                 160

Ile Pro Trp Asn Leu Glu Arg Ile Thr Pro Pro Arg Tyr Arg Ala Asp
                165                 170                 175

Glu Tyr Gln Pro Pro Asp Gly Gly Ser Leu Val Glu Val Tyr Leu Leu
            180                 185                 190

Asp Thr Ser Ile Gln Ser Asp His Arg Glu Ile Glu Gly Arg Val Met
        195                 200                 205

Val Thr Asp Phe Glu Asn Val Pro Glu Glu Asp Gly Thr Arg Phe His
    210                 215                 220
```

```
Arg Gln Ala Ser Lys Cys Asp Ser His Gly Thr His Leu Ala Gly Val
225                 230                 235                 240

Val Ser Gly Arg Asp Ala Gly Val Ala Lys Gly Ala Ser Met Arg Ser
            245                 250                 255

Leu Arg Val Leu Asn Cys Gln Gly Lys Gly Thr Val Ser Gly Thr Leu
                260                 265                 270

Ile Gly Leu Glu Phe Ile Arg Lys Ser Gln Leu Val Gln Pro Val Gly
            275                 280                 285

Pro Leu Val Val Leu Leu Pro Leu Ala Gly Gly Tyr Ser Arg Val Leu
            290                 295                 300

Asn Ala Ala Cys Gln Arg Leu Ala Arg Ala Gly Val Val Leu Val Thr
305                 310                 315                 320

Ala Ala Gly Asn Phe Arg Asp Asp Ala Cys Leu Tyr Ser Pro Ala Ser
                325                 330                 335

Ala Pro Glu Val Ile Thr Val Gly Ala Thr Asn Ala Gln Asp Gln Pro
            340                 345                 350

Val Thr Leu Gly Thr Leu Gly Thr Asn Phe Gly Arg Cys Val Asp Leu
            355                 360                 365

Phe Ala Pro Gly Glu Asp Ile Ile Gly Ala Ser Ser Asp Cys Ser Thr
370                 375                 380

Cys Phe Val Ser Gln Ser Gly Thr Ser Gln Ala Ala His Val Ala
385                 390                 395                 400

Gly Ile Ala Ala Met Met Leu Ser Ala Glu Pro Glu Leu Thr Leu Ala
                405                 410                 415

Glu Leu Arg Gln Arg Leu Ile His Phe Ser Ala Lys Asp Val Ile Asn
            420                 425                 430

Glu Ala Trp Phe Pro Glu Asp Gln Arg Val Leu Thr Pro Asn Leu Val
            435                 440                 445

Ala Ala Leu Pro Pro Ser Thr His Gly Ala Gly Trp Gln Leu Phe Cys
450                 455                 460

Arg Thr Val Trp Ser Ala His Ser Gly Pro Thr Arg Met Ala Thr Ala
465                 470                 475                 480

Ile Ala Arg Cys Ala Pro Asp Glu Glu Leu Leu Ser Cys Ser Ser Phe
                485                 490                 495

Ser Arg Ser Gly Lys Arg Arg Gly Glu Arg Met Glu Ala Gln Gly Gly
            500                 505                 510

Lys Leu Val Cys Arg Ala His Asn Ala Phe Gly Gly Glu Gly Val Tyr
            515                 520                 525

Ala Ile Ala Arg Cys Cys Leu Leu Pro Gln Ala Asn Cys Ser Val His
530                 535                 540

Thr Ala Pro Pro Ala Glu Ala Ser Met Gly Thr Arg Val His Cys His
545                 550                 555                 560

Gln Gln Gly His Val Leu Thr Gly Cys Ser Ser His Trp Glu Val Glu
                565                 570                 575

Asp Leu Gly Thr His Lys Pro Pro Val Leu Arg Pro Arg Gly Gln Pro
            580                 585                 590

Asn Gln Cys Val Gly His Arg Glu Ala Ser Ile His Ala Ser Cys Cys
                595                 600                 605

His Ala Pro Gly Leu Glu Cys Lys Val Lys Glu His Gly Ile Pro Ala
            610                 615                 620

Pro Gln Glu Gln Val Thr Val Ala Cys Glu Glu Gly Trp Thr Leu Thr
625                 630                 635                 640

Gly Cys Ser Ala Leu Pro Gly Thr Ser His Val Leu Gly Ala Tyr Ala
```

```
                    645                 650                 655
Val Asp Asn Thr Cys Val Val Arg Ser Arg Asp Val Ser Thr Thr Gly
                660                 665                 670

Ser Thr Ser Glu Glu Ala Val Thr Ala Val Ala Ile Cys Cys Arg Ser
            675                 680                 685

Arg His Leu Ala Gln Ala Ser Gln Glu Leu Gln
        690                 695

<210> SEQ ID NO 12
<211> LENGTH: 744
<212> TYPE: PRT
<213> ORGANISM: Artificial Sequence
<220> FEATURE:
<223> OTHER INFORMATION: PCSK9-152Flag-V5/His

<400> SEQUENCE: 12

Met Gly Thr Val Ser Ser Arg Arg Ser Trp Trp Pro Leu Pro Leu Leu
 1               5                  10                  15

Leu Leu Leu Leu Leu Leu Leu Gly Pro Ala Gly Ala Arg Ala Gln Glu
                20                  25                  30

Asp Glu Asp Gly Asp Tyr Glu Glu Leu Val Leu Ala Leu Arg Ser Glu
            35                  40                  45

Glu Asp Gly Leu Ala Glu Ala Pro Glu His Gly Thr Thr Ala Thr Phe
        50                  55                  60

His Arg Cys Ala Lys Asp Pro Trp Arg Leu Pro Gly Thr Tyr Val Val
 65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Asp Tyr Lys Asp Asp Asp Asp Ser
145                 150                 155                 160

Ile Pro Trp Asn Leu Glu Arg Ile Thr Pro Pro Arg Tyr Arg Ala Asp
                165                 170                 175

Glu Tyr Gln Pro Pro Asp Gly Gly Ser Leu Val Glu Val Tyr Leu Leu
            180                 185                 190

Asp Thr Ser Ile Gln Ser Asp His Arg Glu Ile Glu Gly Arg Val Met
        195                 200                 205

Val Thr Asp Phe Glu Asn Val Pro Glu Glu Asp Gly Thr Arg Phe His
    210                 215                 220

Arg Gln Ala Ser Lys Cys Asp Ser His Gly Thr His Leu Ala Gly Val
225                 230                 235                 240

Val Ser Gly Arg Asp Ala Gly Val Ala Lys Gly Ala Ser Met Arg Ser
                245                 250                 255

Leu Arg Val Leu Asn Cys Gln Gly Lys Gly Thr Val Ser Gly Thr Leu
            260                 265                 270

Ile Gly Leu Glu Phe Ile Arg Lys Ser Gln Leu Val Gln Pro Val Gly
        275                 280                 285

Pro Leu Val Val Leu Leu Pro Leu Ala Gly Gly Tyr Ser Arg Val Leu
    290                 295                 300

Asn Ala Ala Cys Gln Arg Leu Ala Arg Ala Gly Val Val Leu Val Thr
305                 310                 315                 320
```

```
Ala Ala Gly Asn Phe Arg Asp Asp Ala Cys Leu Tyr Ser Pro Ala Ser
            325                 330                 335

Ala Pro Glu Val Ile Thr Val Gly Ala Thr Asn Ala Gln Asp Gln Pro
            340                 345                 350

Val Thr Leu Gly Thr Leu Gly Thr Asn Phe Gly Arg Cys Val Asp Leu
            355                 360                 365

Phe Ala Pro Gly Glu Asp Ile Ile Gly Ala Ser Ser Asp Cys Ser Thr
            370                 375                 380

Cys Phe Val Ser Gln Ser Gly Thr Ser Gln Ala Ala His Val Ala
385                 390                 395                 400

Gly Ile Ala Ala Met Met Leu Ser Ala Glu Pro Glu Leu Thr Leu Ala
                    405                 410                 415

Glu Leu Arg Gln Arg Leu Ile His Phe Ser Ala Lys Asp Val Ile Asn
            420                 425                 430

Glu Ala Trp Phe Pro Glu Asp Gln Arg Val Leu Thr Pro Asn Leu Val
            435                 440                 445

Ala Ala Leu Pro Pro Ser Thr His Gly Ala Gly Trp Gln Leu Phe Cys
            450                 455                 460

Arg Thr Val Trp Ser Ala His Ser Gly Pro Thr Arg Met Ala Thr Ala
465                 470                 475                 480

Ile Ala Arg Cys Ala Pro Asp Glu Glu Leu Leu Ser Cys Ser Ser Phe
                485                 490                 495

Ser Arg Ser Gly Lys Arg Arg Gly Glu Arg Met Glu Ala Gln Gly Gly
            500                 505                 510

Lys Leu Val Cys Arg Ala His Asn Ala Phe Gly Gly Glu Gly Val Tyr
            515                 520                 525

Ala Ile Ala Arg Cys Cys Leu Leu Pro Gln Ala Asn Cys Ser Val His
            530                 535                 540

Thr Ala Pro Pro Ala Glu Ala Ser Met Gly Thr Arg Val His Cys His
545                 550                 555                 560

Gln Gln Gly His Val Leu Thr Gly Cys Ser Ser His Trp Glu Val Glu
                565                 570                 575

Asp Leu Gly Thr His Lys Pro Pro Val Leu Arg Pro Arg Gly Gln Pro
            580                 585                 590

Asn Gln Cys Val Gly His Arg Glu Ala Ser Ile His Ala Ser Cys Cys
            595                 600                 605

His Ala Pro Gly Leu Glu Cys Lys Val Lys Glu His Gly Ile Pro Ala
610                 615                 620

Pro Gln Glu Gln Val Thr Val Ala Cys Glu Glu Gly Trp Thr Leu Thr
625                 630                 635                 640

Gly Cys Ser Ala Leu Pro Gly Thr Ser His Val Leu Gly Ala Tyr Ala
                645                 650                 655

Val Asp Asn Thr Cys Val Val Arg Ser Arg Asp Val Ser Thr Thr Gly
            660                 665                 670

Ser Thr Ser Glu Glu Ala Val Thr Ala Val Ala Ile Cys Cys Arg Ser
            675                 680                 685

Arg His Leu Ala Gln Ala Ser Gln Glu Leu Gln Lys Gly Asn Ser Ala
            690                 695                 700

Asp Ile Gln His Ser Gly Gly Arg Ser Ser Leu Glu Gly Pro Arg Phe
705                 710                 715                 720

Glu Gly Lys Pro Ile Pro Asn Pro Leu Leu Gly Leu Asp Ser Thr Arg
                725                 730                 735

Thr Gly His His His His His His
```

<210> SEQ ID NO 13
<211> LENGTH: 11
<212> TYPE: PRT
<213> ORGANISM: Artificial Sequence
<220> FEATURE:
<223> OTHER INFORMATION: HA Epitope with additional amino acids

<400> SEQUENCE: 13

```
Gln Glu Tyr Pro Tyr Asp Val Pro Asp Tyr Ala
 1               5                  10
```

<210> SEQ ID NO 14
<211> LENGTH: 67
<212> TYPE: DNA
<213> ORGANISM: Artificial Sequence
<220> FEATURE:
<223> OTHER INFORMATION: PCR primer

<400> SEQUENCE: 14
ccgcgggcgc ccgtgcgcag gaatacccett atgatgttcc tgattatgcc caggaggacg    60
aggacgg    67

<210> SEQ ID NO 15
<211> LENGTH: 67
<212> TYPE: DNA
<213> ORGANISM: Artificial Sequence
<220> FEATURE:
<223> OTHER INFORMATION: PCR primer

<400> SEQUENCE: 15
ccgtcctcgt cctcctgggc ataatcagga acatcataag ggtattcctg cgcacgggcg    60
cccgcgg    67

<210> SEQ ID NO 16
<211> LENGTH: 710
<212> TYPE: PRT
<213> ORGANISM: Artificial Sequence
<220> FEATURE:
<223> OTHER INFORMATION: PCSK9-30HA-152Flag

<400> SEQUENCE: 16

```
Met Gly Thr Val Ser Ser Arg Arg Ser Trp Trp Pro Leu Pro Leu Leu
 1               5                  10                  15

Leu Leu Leu Leu Leu Leu Leu Gly Pro Ala Gly Ala Arg Ala Gln Glu
                20                  25                  30

Tyr Pro Tyr Asp Val Pro Asp Tyr Ala Gln Glu Asp Glu Asp Gly Asp
            35                  40                  45

Tyr Glu Glu Leu Val Leu Ala Leu Arg Ser Glu Glu Asp Gly Leu Ala
        50                  55                  60

Glu Ala Pro Glu His Gly Thr Thr Ala Thr Phe His Arg Cys Ala Lys
 65                  70                  75                  80

Asp Pro Trp Arg Leu Pro Gly Thr Tyr Val Val Val Leu Lys Glu Glu
                85                  90                  95

Thr His Leu Ser Gln Ser Glu Arg Thr Ala Arg Arg Leu Gln Ala Gln
               100                 105                 110

Ala Ala Arg Arg Gly Tyr Leu Thr Lys Ile Leu His Val Phe His Gly
           115                 120                 125

Leu Leu Pro Gly Phe Leu Val Lys Met Ser Gly Asp Leu Leu Glu Leu
       130                 135                 140
```

```
Ala Leu Lys Leu Pro His Val Asp Tyr Ile Glu Glu Asp Ser Ser Val
145                 150                 155                 160

Phe Ala Gln Asp Tyr Lys Asp Asp Asp Ser Ile Pro Trp Asn Leu
            165                 170                 175

Glu Arg Ile Thr Pro Pro Arg Tyr Arg Ala Asp Glu Tyr Gln Pro Pro
            180                 185                 190

Asp Gly Gly Ser Leu Val Glu Val Tyr Leu Leu Asp Thr Ser Ile Gln
            195                 200                 205

Ser Asp His Arg Glu Ile Glu Gly Arg Val Met Val Thr Asp Phe Glu
210                 215                 220

Asn Val Pro Glu Glu Asp Gly Thr Arg Phe His Arg Gln Ala Ser Lys
225                 230                 235                 240

Cys Asp Ser His Gly Thr His Leu Ala Gly Val Val Ser Gly Arg Asp
            245                 250                 255

Ala Gly Val Ala Lys Gly Ala Ser Met Arg Ser Leu Arg Val Leu Asn
            260                 265                 270

Cys Gln Gly Lys Gly Thr Val Ser Gly Thr Leu Ile Gly Leu Glu Phe
            275                 280                 285

Ile Arg Lys Ser Gln Leu Val Gln Pro Val Gly Pro Leu Val Val Leu
290                 295                 300

Leu Pro Leu Ala Gly Gly Tyr Ser Arg Val Leu Asn Ala Ala Cys Gln
305                 310                 315                 320

Arg Leu Ala Arg Ala Gly Val Val Leu Val Thr Ala Ala Gly Asn Phe
            325                 330                 335

Arg Asp Asp Ala Cys Leu Tyr Ser Pro Ala Ser Ala Pro Glu Val Ile
            340                 345                 350

Thr Val Gly Ala Thr Asn Ala Gln Asp Gln Pro Val Thr Leu Gly Thr
            355                 360                 365

Leu Gly Thr Asn Phe Gly Arg Cys Val Asp Leu Phe Ala Pro Gly Glu
370                 375                 380

Asp Ile Ile Gly Ala Ser Ser Asp Cys Ser Thr Cys Phe Val Ser Gln
385                 390                 395                 400

Ser Gly Thr Ser Gln Ala Ala Ala His Val Ala Gly Ile Ala Ala Met
            405                 410                 415

Met Leu Ser Ala Glu Pro Glu Leu Thr Leu Ala Glu Leu Arg Gln Arg
            420                 425                 430

Leu Ile His Phe Ser Ala Lys Asp Val Ile Asn Glu Ala Trp Phe Pro
            435                 440                 445

Glu Asp Gln Arg Val Leu Thr Pro Asn Leu Val Ala Ala Leu Pro Pro
450                 455                 460

Ser Thr His Gly Ala Gly Trp Gln Leu Phe Cys Arg Thr Val Trp Ser
465                 470                 475                 480

Ala His Ser Gly Pro Thr Arg Met Ala Thr Ala Ile Ala Arg Cys Ala
            485                 490                 495

Pro Asp Glu Glu Leu Leu Ser Cys Ser Ser Phe Ser Arg Ser Gly Lys
            500                 505                 510

Arg Arg Gly Glu Arg Met Glu Ala Gln Gly Gly Lys Leu Val Cys Arg
            515                 520                 525

Ala His Asn Ala Phe Gly Gly Glu Gly Val Tyr Ala Ile Ala Arg Cys
            530                 535                 540

Cys Leu Leu Pro Gln Ala Asn Cys Ser Val His Thr Ala Pro Pro Ala
545                 550                 555                 560

Glu Ala Ser Met Gly Thr Arg Val His Cys His Gln Gln Gly His Val
            565                 570                 575
```

```
Leu Thr Gly Cys Ser Ser His Trp Glu Val Glu Asp Leu Gly Thr His
                580                 585                 590

Lys Pro Pro Val Leu Arg Pro Arg Gly Gln Pro Asn Gln Cys Val Gly
            595                 600                 605

His Arg Glu Ala Ser Ile His Ala Ser Cys Cys His Ala Pro Gly Leu
        610                 615                 620

Glu Cys Lys Val Lys Glu His Gly Ile Pro Ala Pro Gln Glu Gln Val
625                 630                 635                 640

Thr Val Ala Cys Glu Glu Gly Trp Thr Leu Thr Gly Cys Ser Ala Leu
                645                 650                 655

Pro Gly Thr Ser His Val Leu Gly Ala Tyr Ala Val Asp Asn Thr Cys
            660                 665                 670

Val Val Arg Ser Arg Asp Val Ser Thr Thr Gly Ser Thr Ser Glu Glu
        675                 680                 685

Ala Val Thr Ala Val Ala Ile Cys Cys Arg Ser Arg His Leu Ala Gln
690                 695                 700

Ala Ser Gln Glu Leu Gln
705             710

<210> SEQ ID NO 17
<211> LENGTH: 8
<212> TYPE: PRT
<213> ORGANISM: Artificial Sequence
<220> FEATURE:
<223> OTHER INFORMATION: HA Epitope

<400> SEQUENCE: 17

Tyr Pro Tyr Asp Val Pro Asp Tyr
1               5

<210> SEQ ID NO 18
<211> LENGTH: 694
<212> TYPE: PRT
<213> ORGANISM: murine

<400> SEQUENCE: 18

Met Gly Thr His Cys Ser Ala Trp Leu Arg Trp Pro Leu Leu Pro Leu
1               5                   10                  15

Leu Pro Pro Leu Leu Leu Leu Leu Leu Leu Cys Pro Thr Gly Ala
            20                  25                  30

Gly Ala Gln Asp Glu Asp Gly Asp Tyr Glu Glu Leu Met Leu Ala Leu
        35                  40                  45

Pro Ser Gln Glu Asp Gly Leu Ala Asp Glu Ala Ala His Val Ala Thr
50                  55                  60

Ala Thr Phe Arg Arg Cys Ser Lys Glu Ala Trp Arg Leu Pro Gly Thr
65                  70                  75                  80

Tyr Ile Val Val Leu Met Glu Glu Thr Gln Arg Leu Gln Ile Glu Gln
                85                  90                  95

Thr Ala His Arg Leu Gln Thr Arg Ala Ala Arg Arg Gly Tyr Val Ile
            100                 105                 110

Lys Val Leu His Ile Phe Tyr Asp Leu Phe Pro Gly Phe Leu Val Lys
        115                 120                 125

Met Ser Ser Asp Leu Leu Gly Leu Ala Leu Lys Leu Pro His Val Glu
130                 135                 140

Tyr Ile Glu Glu Asp Ser Phe Val Phe Ala Gln Ser Ile Pro Trp Asn
145                 150                 155                 160

Leu Glu Arg Ile Ile Pro Ala Trp His Gln Thr Glu Glu Asp Arg Ser
```

-continued

```
                165                 170                 175
Pro Asp Gly Ser Ser Gln Val Glu Val Tyr Leu Leu Asp Thr Ser Ile
            180                 185                 190
Gln Gly Ala His Arg Glu Ile Glu Gly Arg Val Thr Ile Thr Asp Phe
            195                 200                 205
Asn Ser Val Pro Glu Glu Asp Gly Thr Arg Phe His Arg Gln Ala Ser
            210                 215                 220
Lys Cys Asp Ser His Gly Thr His Leu Ala Gly Val Val Ser Gly Arg
225                 230                 235                 240
Asp Ala Gly Val Ala Lys Gly Thr Ser Leu His Ser Leu Arg Val Leu
                245                 250                 255
Asn Cys Gln Gly Lys Gly Thr Val Ser Gly Thr Leu Ile Gly Leu Glu
            260                 265                 270
Phe Ile Arg Lys Ser Gln Leu Ile Gln Pro Ser Gly Pro Leu Val Val
            275                 280                 285
Leu Leu Pro Leu Ala Gly Gly Tyr Ser Arg Ile Leu Asn Ala Ala Cys
            290                 295                 300
Arg His Leu Ala Arg Thr Gly Val Val Leu Val Ala Ala Ala Gly Asn
305                 310                 315                 320
Phe Arg Asp Asp Ala Cys Leu Tyr Ser Pro Ala Ser Ala Pro Glu Val
                325                 330                 335
Ile Thr Val Gly Ala Thr Asn Ala Gln Asp Gln Pro Val Thr Leu Gly
            340                 345                 350
Thr Leu Gly Thr Asn Phe Gly Arg Cys Val Asp Leu Phe Ala Pro Gly
            355                 360                 365
Lys Asp Ile Ile Gly Ala Ser Ser Asp Cys Ser Thr Cys Phe Met Ser
370                 375                 380
Gln Ser Gly Thr Ser Gln Ala Ala Ala His Val Ala Gly Ile Val Ala
385                 390                 395                 400
Arg Met Leu Ser Arg Glu Pro Thr Leu Thr Leu Ala Glu Leu Arg Gln
                405                 410                 415
Arg Leu Ile His Phe Ser Thr Lys Asp Val Ile Asn Met Ala Trp Phe
            420                 425                 430
Pro Glu Asp Gln Gln Val Leu Thr Pro Asn Leu Val Ala Thr Leu Pro
            435                 440                 445
Pro Ser Thr His Glu Thr Gly Gly Gln Leu Leu Cys Arg Thr Val Trp
            450                 455                 460
Ser Ala His Ser Gly Pro Thr Arg Thr Ala Thr Ala Thr Ala Arg Cys
465                 470                 475                 480
Ala Pro Glu Glu Glu Leu Leu Ser Cys Ser Ser Phe Ser Arg Ser Gly
                485                 490                 495
Arg Arg Arg Gly Asp Trp Ile Glu Ala Ile Gly Gly Gln Gln Val Cys
            500                 505                 510
Lys Ala Leu Asn Ala Phe Gly Gly Glu Gly Val Tyr Ala Val Ala Arg
            515                 520                 525
Cys Cys Leu Val Pro Arg Ala Asn Cys Ser Ile His Asn Thr Pro Ala
            530                 535                 540
Ala Arg Ala Gly Leu Glu Thr His Val His Cys His Gln Lys Asp His
545                 550                 555                 560
Val Leu Thr Gly Cys Ser Phe His Trp Glu Val Glu Asp Leu Ser Val
                565                 570                 575
Arg Arg Gln Pro Ala Leu Arg Ser Arg Arg Gln Pro Gly Gln Cys Val
            580                 585                 590
```

-continued

Gly His Gln Ala Ala Ser Val Tyr Ala Ser Cys Cys His Ala Pro Gly
            595                 600                 605

Leu Glu Cys Lys Ile Lys Glu His Gly Ile Ser Gly Pro Ser Glu Gln
    610                 615                 620

Val Thr Val Ala Cys Glu Ala Gly Trp Thr Leu Thr Gly Cys Asn Val
625                 630                 635                 640

Leu Pro Gly Ala Ser Leu Thr Leu Gly Ala Tyr Ser Val Asp Asn Leu
                645                 650                 655

Cys Val Ala Arg Val His Asp Thr Ala Arg Ala Asp Arg Thr Ser Gly
            660                 665                 670

Glu Ala Thr Val Ala Ala Ile Cys Cys Arg Ser Arg Pro Ser Ala
    675                 680                 685

Lys Ala Ser Trp Val Gln
    690

<210> SEQ ID NO 19
<211> LENGTH: 691
<212> TYPE: PRT
<213> ORGANISM: rattus norvegicus

<400> SEQUENCE: 19

Met Gly Ile Arg Cys Ser Thr Trp Leu Arg Trp Pro Leu Ser Pro Gln
1               5                   10                  15

Leu Leu Leu Leu Leu Leu Cys Pro Thr Gly Ser Arg Ala Gln Asp
            20                  25                  30

Glu Asp Gly Asp Tyr Glu Glu Leu Met Leu Ala Leu Pro Ser Gln Glu
            35                  40                  45

Asp Ser Leu Val Asp Glu Ala Ser His Val Ala Thr Ala Thr Phe Arg
50                  55                  60

Arg Cys Ser Lys Glu Ala Trp Arg Leu Pro Gly Thr Tyr Val Val Val
65                  70                  75                  80

Leu Met Glu Glu Thr Gln Arg Leu Gln Val Gln Thr Ala His Arg
            85                  90                  95

Leu Gln Thr Trp Ala Ala Arg Arg Gly Tyr Val Ile Lys Val Leu His
            100                 105                 110

Val Phe Tyr Asp Leu Phe Pro Gly Phe Leu Val Lys Met Ser Ser Asp
            115                 120                 125

Leu Leu Gly Leu Ala Leu Lys Leu Pro His Val Glu Tyr Ile Glu Glu
            130                 135                 140

Asp Ser Leu Val Phe Ala Gln Ser Ile Pro Trp Asn Leu Glu Arg Ile
145                 150                 155                 160

Ile Pro Ala Trp Gln Gln Thr Glu Glu Asp Ser Ser Pro Asp Gly Ser
                165                 170                 175

Ser Gln Val Glu Val Tyr Leu Leu Asp Thr Ser Ile Gln Ser Gly His
            180                 185                 190

Arg Glu Ile Glu Gly Arg Val Thr Ile Thr Asp Phe Asn Ser Val Pro
            195                 200                 205

Glu Glu Asp Gly Thr Arg Phe His Arg Gln Ala Ser Lys Cys Asp Ser
    210                 215                 220

His Gly Thr His Leu Ala Gly Val Val Ser Gly Arg Asp Ala Gly Val
225                 230                 235                 240

Ala Lys Gly Thr Ser Leu His Ser Leu Arg Val Leu Asn Cys Gln Gly
                245                 250                 255

Lys Gly Thr Val Ser Gly Thr Leu Ile Gly Leu Glu Phe Ile Arg Lys
            260                 265                 270

```
Ser Gln Leu Ile Gln Pro Ser Pro Leu Val Val Leu Pro Leu
    275                 280                 285

Ala Gly Gly Tyr Ser Arg Ile Leu Asn Thr Ala Cys Gln Arg Leu Ala
290                     295                 300

Arg Thr Gly Val Val Leu Val Ala Ala Gly Asn Phe Arg Asp Asp
305                 310                 315                 320

Ala Cys Leu Tyr Ser Pro Ala Ser Ala Pro Glu Val Ile Thr Val Gly
                325                 330                 335

Ala Thr Asn Ala Gln Asp Gln Pro Val Thr Leu Gly Thr Leu Gly Thr
            340                 345                 350

Asn Phe Gly Arg Cys Val Asp Leu Phe Ala Pro Gly Lys Asp Ile Ile
            355                 360                 365

Gly Ala Ser Ser Asp Cys Ser Thr Cys Tyr Met Ser Gln Ser Gly Thr
370                 375                 380

Ser Gln Ala Ala Ala His Val Ala Gly Ile Val Ala Met Met Leu Asn
385                 390                 395                 400

Arg Asp Pro Ala Leu Thr Leu Ala Glu Leu Arg Gln Arg Leu Ile Leu
                405                 410                 415

Phe Ser Thr Lys Asp Val Ile Asn Met Ala Trp Phe Pro Glu Asp Gln
                420                 425                 430

Arg Val Leu Thr Pro Asn Arg Val Ala Thr Leu Pro Pro Ser Thr Gln
            435                 440                 445

Glu Thr Gly Gly Gln Leu Leu Cys Arg Thr Val Trp Ser Ala His Ser
450                 455                 460

Gly Pro Thr Arg Thr Ala Thr Ala Thr Ala Arg Cys Ala Pro Glu Glu
465                 470                 475                 480

Glu Leu Leu Ser Cys Ser Ser Phe Ser Arg Ser Gly Arg Arg Gly
                485                 490                 495

Asp Arg Ile Glu Ala Ile Gly Gly Gln Gln Val Cys Lys Ala Leu Asn
                500                 505                 510

Ala Phe Gly Gly Glu Gly Val Tyr Ala Val Ala Arg Cys Cys Leu Leu
            515                 520                 525

Pro Arg Val Asn Cys Ser Ile His Asn Thr Pro Ala Ala Arg Ala Gly
            530                 535                 540

Pro Gln Thr Pro Val His Cys His Gln Lys Asp His Val Leu Thr Gly
545                 550                 555                 560

Cys Ser Phe His Trp Glu Val Glu Asn Leu Arg Ala Gln Gln Pro
                565                 570                 575

Leu Leu Arg Ser Arg His Gln Pro Gly Gln Cys Val Gly His Gln Glu
            580                 585                 590

Ala Ser Val His Ala Ser Cys Cys His Ala Pro Gly Leu Glu Cys Lys
            595                 600                 605

Ile Lys Glu His Gly Ile Ala Gly Pro Ala Glu Gln Val Thr Val Ala
        610                 615                 620

Cys Glu Ala Gly Trp Thr Leu Thr Gly Cys Asn Val Leu Pro Gly Ala
625                 630                 635                 640

Ser Leu Pro Leu Gly Ala Tyr Ser Val Asp Asn Val Cys Val Ala Arg
                645                 650                 655

Ile Arg Asp Ala Gly Arg Ala Asp Arg Thr Ser Glu Glu Ala Thr Val
            660                 665                 670

Ala Ala Ala Ile Cys Cys Arg Ser Arg Pro Ser Ala Lys Ala Ser Trp
            675                 680                 685

Val His Gln
    690
```

<210> SEQ ID NO 20
<211> LENGTH: 122
<212> TYPE: PRT
<213> ORGANISM: Artificial Sequence
<220> FEATURE:
<223> OTHER INFORMATION: PCSK9 pro domain

<400> SEQUENCE: 20

```
Gln Glu Asp Glu Asp Gly Asp Tyr Glu Glu Leu Val Leu Ala Leu Arg
  1               5                  10                  15

Ser Glu Glu Asp Gly Leu Ala Glu Ala Pro Glu His Gly Thr Thr Ala
             20                  25                  30

Thr Phe His Arg Cys Ala Lys Asp Pro Trp Arg Leu Pro Gly Thr Tyr
         35                  40                  45

Val Val Val Leu Lys Glu Glu Thr His Leu Ser Gln Ser Glu Arg Thr
     50                  55                  60

Ala Arg Arg Leu Gln Ala Gln Ala Ala Arg Arg Gly Tyr Leu Thr Lys
 65                  70                  75                  80

Ile Leu His Val Phe His Gly Leu Leu Pro Gly Phe Leu Val Lys Met
                 85                  90                  95

Ser Gly Asp Leu Leu Glu Leu Ala Leu Lys Leu Pro His Val Asp Tyr
            100                 105                 110

Ile Glu Glu Asp Ser Ser Val Phe Ala Gln
            115                 120
```

<210> SEQ ID NO 21
<211> LENGTH: 32
<212> TYPE: DNA
<213> ORGANISM: Artificial Sequence
<220> FEATURE:
<223> OTHER INFORMATION: PCR primer

<400> SEQUENCE: 21
cacagagtgg gacagcacag gctgctgccc ac        32

<210> SEQ ID NO 22
<211> LENGTH: 31
<212> TYPE: DNA
<213> ORGANISM: Artificial Sequence
<220> FEATURE:
<223> OTHER INFORMATION: PCR primer

<400> SEQUENCE: 22
gtgggcagca gcctgtgctg tcccactcgt g        31

<210> SEQ ID NO 23
<211> LENGTH: 35
<212> TYPE: DNA
<213> ORGANISM: Artificial Sequence
<220> FEATURE:
<223> OTHER INFORMATION: PCR primer

<400> SEQUENCE: 23
ggaggtgtat ctcctagcca ccagcataca gagtg        35

<210> SEQ ID NO 24
<211> LENGTH: 35
<212> TYPE: DNA
<213> ORGANISM: Artificial Sequence
<220> FEATURE:
<223> OTHER INFORMATION: PCR primer

<400> SEQUENCE: 24

-continued

```
cactctgtat gctggtggct aggagataca cctcc                                35
```

<210> SEQ ID NO 25
<211> LENGTH: 489
<212> TYPE: DNA
<213> ORGANISM: Artificial Sequence
<220> FEATURE:
<223> OTHER INFORMATION: pro plasmid insert

<400> SEQUENCE: 25

```
atgggcaccg tcagctccag gcggtcctgg tggccgctgc cactgctgct gctgctgctg    60
ctgctcctgg gtcccgcggg cgcccgtgcg caggagtacc cttatgatgt tcctgattat   120
gcccaggagg acgaggacgg cgactacgag gagctggtgc tagccttgcg ttccgaggag   180
gacggcctgg ccgaagcacc cgagcacgga accacagcca ccttccaccg ctgcgccaag   240
gatccgtgga ggttgcctgg cacctacgtg gtggtgctga aggaggagac ccacctctcg   300
cagtcagagc gcactgcccg ccgcctgcag gcccaggctg cccgccgggg atacctcacc   360
aagatcctgc atgtcttcca tggccttctt cctggcttcc tggtgaagat gagtggcgac   420
ctgctggagc tggccttgaa gttgccccat gtcgactaca tcgaggagga ctcctctgtc   480
tttgcccag                                                           489
```

<210> SEQ ID NO 26
<211> LENGTH: 163
<212> TYPE: PRT
<213> ORGANISM: Artificial Sequence
<220> FEATURE:
<223> OTHER INFORMATION: pro plasmid insert

<400> SEQUENCE: 26

Met Gly Thr Val Ser Ser Arg Arg Ser Trp Trp Pro Leu Pro Leu Leu
1               5                   10                  15

Leu Leu Leu Leu Leu Leu Gly Pro Ala Gly Ala Arg Ala Gln Glu
            20                  25                  30

Tyr Pro Tyr Asp Val Pro Asp Tyr Ala Gln Glu Asp Glu Asp Gly Asp
        35                  40                  45

Tyr Glu Glu Leu Val Leu Ala Leu Arg Ser Glu Glu Asp Gly Leu Ala
    50                  55                  60

Glu Ala Pro Glu His Gly Thr Thr Ala Thr Phe His Arg Cys Ala Lys
65                  70                  75                  80

Asp Pro Trp Arg Leu Pro Gly Thr Tyr Val Val Val Leu Lys Glu Glu
                85                  90                  95

Thr His Leu Ser Gln Ser Glu Arg Thr Ala Arg Arg Leu Gln Ala Gln
            100                 105                 110

Ala Ala Arg Arg Gly Tyr Leu Thr Lys Ile Leu His Val Phe His Gly
        115                 120                 125

Leu Leu Pro Gly Phe Leu Val Lys Met Ser Gly Asp Leu Leu Glu Leu
    130                 135                 140

Ala Leu Lys Leu Pro His Val Asp Tyr Ile Glu Glu Asp Ser Ser Val
145                 150                 155                 160

Phe Ala Gln

<210> SEQ ID NO 27
<211> LENGTH: 6
<212> TYPE: PRT
<213> ORGANISM: Artificial Sequence
<220> FEATURE:
<223> OTHER INFORMATION: figure 6

```
<400> SEQUENCE: 27

Ala Arg Ala Gln Glu Asp
1               5

<210> SEQ ID NO 28
<211> LENGTH: 9
<212> TYPE: PRT
<213> ORGANISM: Artificial Sequence
<220> FEATURE:
<223> OTHER INFORMATION: figure 6

<400> SEQUENCE: 28

Ser Ser Val Phe Ala Gln Ser Ile Pro
1               5

<210> SEQ ID NO 29
<211> LENGTH: 16
<212> TYPE: PRT
<213> ORGANISM: Artificial Sequence
<220> FEATURE:
<223> OTHER INFORMATION: figure 6

<400> SEQUENCE: 29

Ser Ser Val Phe Ala Gln Asp Tyr Lys Asp Asp Asp Asp Ser Ile Pro
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: figure 8

<400> SEQUENCE: 30

Ser Val Phe Ala Gln Asp Tyr Lys Asp Asp Asp Asp Ser Ile Pro Trp
1               5                   10                  15

<210> SEQ ID NO 31
<211> LENGTH: 5
<212> TYPE: PRT
<213> ORGANISM: Artificial Sequence
<220> FEATURE:
<223> OTHER INFORMATION: figure 8

<400> SEQUENCE: 31

Ser Val Phe Ala Gln
1               5

<210> SEQ ID NO 32
<211> LENGTH: 11
<212> TYPE: PRT
<213> ORGANISM: Artificial Sequence
<220> FEATURE:
<223> OTHER INFORMATION: figure 8

<400> SEQUENCE: 32

Asp Tyr Lys Asp Asp Asp Asp Ser Ile Pro Trp
1               5                   10

<210> SEQ ID NO 33
<211> LENGTH: 366
<212> TYPE: DNA
<213> ORGANISM: Artificial Sequence
<220> FEATURE:
<223> OTHER INFORMATION: PCSK9 pro domain

<400> SEQUENCE: 33
```

```
caggaggacg aggacggcga ctacgaggag ctggtgctag ccttgcgttc cgaggaggac      60
ggcctggccg aagcacccga gcacggaacc acagccacct tccaccgctg cgccaaggat     120
ccgtggaggt tgcctggcac ctacgtggtg gtgctgaagg aggagaccca cctctcgcag     180
tcagagcgca ctgcccgccg cctgcaggcc caggctgccc gccggggata cctcaccaag     240
atcctgcatg tcttccatgg ccttcttcct ggcttcctgg tgaagatgag tggcgacctg     300
ctggagctgg ccttgaagtt gccccatgtc gactacatcg aggaggactc ctctgtcttt     360
gcccag                                                                366
```

```
<210> SEQ ID NO 34
<211> LENGTH: 692
<212> TYPE: PRT
<213> ORGANISM: Artificial Sequence
<220> FEATURE:
<223> OTHER INFORMATION: D186 A PCSK9

<400> SEQUENCE: 34
```

Met Gly Thr Val Ser Ser Arg Arg Ser Trp Trp Pro Leu Pro Leu Leu
 1               5                  10                  15

Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Ala Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu

```
                290                 295                 300
Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
    370                 375                 380

Thr Ser Gln Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
    450                 455                 460

Ser Gly Pro Thr Arg Met Ala Thr Ala Ile Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
    530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Glu Ala Val
            660                 665                 670

Thr Ala Val Ala Ile Cys Cys Arg Ser Arg His Leu Ala Gln Ala Ser
        675                 680                 685

Gln Glu Leu Gln
    690

<210> SEQ ID NO 35
<211> LENGTH: 692
```

```
<212> TYPE: PRT
<213> ORGANISM: Artificial Sequence
<220> FEATURE:
<223> OTHER INFORMATION: S 386 A PCSK9

<400> SEQUENCE: 35

Met Gly Thr Val Ser Ser Arg Arg Ser Trp Trp Pro Leu Pro Leu Leu
 1               5                  10                  15

Leu Leu Leu Leu Leu Leu Leu Gly Pro Ala Gly Ala Arg Ala Gln Glu
             20                  25                  30

Asp Glu Asp Gly Asp Tyr Glu Glu Leu Val Leu Ala Leu Arg Ser Glu
         35                  40                  45

Glu Asp Gly Leu Ala Glu Ala Pro Glu His Gly Thr Thr Ala Thr Phe
     50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                 85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
370                 375                 380

Thr Ala Gln Ala Ala Ala His Val Ala Gly Ile Ala Ala Met Met Leu
```

```
                385              390              395              400
Ser Ala Glu Pro Glu Leu Thr Leu Ala Glu Leu Arg Gln Arg Leu Ile
                    405                  410                  415

His Phe Ser Ala Lys Asp Val Ile Asn Glu Ala Trp Phe Pro Glu Asp
        420                  425                  430

Gln Arg Val Leu Thr Pro Asn Leu Val Ala Ala Leu Pro Pro Ser Thr
            435                  440                  445

His Gly Ala Gly Trp Gln Leu Phe Cys Arg Thr Val Trp Ser Ala His
        450                  455                  460

Ser Gly Pro Thr Arg Met Ala Thr Ala Ile Ala Arg Cys Ala Pro Asp
465                  470                  475                  480

Glu Glu Leu Leu Ser Cys Ser Ser Phe Ser Arg Ser Gly Lys Arg Arg
                    485                  490                  495

Gly Glu Arg Met Glu Ala Gln Gly Gly Lys Leu Val Cys Arg Ala His
                500                  505                  510

Asn Ala Phe Gly Gly Glu Gly Val Tyr Ala Ile Ala Arg Cys Cys Leu
            515                  520                  525

Leu Pro Gln Ala Asn Cys Ser Val His Thr Ala Pro Pro Ala Glu Ala
        530                  535                  540

Ser Met Gly Thr Arg Val His Cys His Gln Gln Gly His Val Leu Thr
545                  550                  555                  560

Gly Cys Ser Ser His Trp Glu Val Glu Asp Leu Gly Thr His Lys Pro
                    565                  570                  575

Pro Val Leu Arg Pro Arg Gly Gln Pro Asn Gln Cys Val Gly His Arg
                580                  585                  590

Glu Ala Ser Ile His Ala Ser Cys Cys His Ala Pro Gly Leu Glu Cys
            595                  600                  605

Lys Val Lys Glu His Gly Ile Pro Ala Pro Gln Glu Gln Val Thr Val
        610                  615                  620

Ala Cys Glu Glu Gly Trp Thr Leu Thr Gly Cys Ser Ala Leu Pro Gly
625                  630                  635                  640

Thr Ser His Val Leu Gly Ala Tyr Ala Val Asp Asn Thr Cys Val Val
                    645                  650                  655

Arg Ser Arg Asp Val Ser Thr Thr Gly Ser Thr Ser Glu Glu Ala Val
                660                  665                  670

Thr Ala Val Ala Ile Cys Cys Arg Ser Arg His Leu Ala Gln Ala Ser
            675                  680                  685

Gln Glu Leu Gln
        690

<210> SEQ ID NO 36
<211> LENGTH: 6
<212> TYPE: PRT
<213> ORGANISM: Artificial Sequence
<220> FEATURE:
<223> OTHER INFORMATION: processing motif

<400> SEQUENCE: 36

Ser Ile Pro Trp Asn Leu
1               5
```